(12) United States Patent
Domb

(10) Patent No.: US 6,958,325 B2
(45) Date of Patent: *Oct. 25, 2005

(54) CATIONIC POLYSACCHARIDE COMPOSITIONS

(75) Inventor: Abraham J. Domb, Efrat (IL)

(73) Assignee: Efrat Biopolymers Limited, Efrat (IL)

( * ) Notice: Subject to any disclaimer, the term of this patent is extended or adjusted under 35 U.S.C. 154(b) by 279 days.

This patent is subject to a terminal disclaimer.

(21) Appl. No.: 10/044,538

(22) Filed: Jan. 10, 2002

(65) Prior Publication Data

US 2002/0146826 A1 Oct. 10, 2002

(30) Foreign Application Priority Data

Jan. 10, 2001 (IL) .................................................. 140844

(51) Int. Cl.$^7$ ........................ C12N 15/85; C07H 21/04; C08B 37/00; C07K 14/435
(52) U.S. Cl. ...................... 514/54; 536/23.1; 536/55.1; 530/395; 435/455
(58) Field of Search .............................. 536/23.1, 55.1, 536/1.11, 112, 123.1, 124; 514/54, 23, 55, 56, 57, 59; 435/455

(56) References Cited

U.S. PATENT DOCUMENTS

| | | | |
|---|---|---|---|
| 3,225,012 A | 12/1965 | Black et al. | |
| 4,146,515 A | 3/1979 | Buikema et al. | |
| 5,312,967 A | 5/1994 | Kieley et al. | |
| 5,329,044 A | 7/1994 | Kieley et al. | |
| 5,434,233 A | 7/1995 | Kieley et al. | |
| 5,473,035 A | 12/1995 | Kieley et al. | |
| 5,833,230 A | 11/1998 | Nakagawa et al. | |

FOREIGN PATENT DOCUMENTS

| | | | |
|---|---|---|---|
| EP | 0 370 810 | 11/1989 | |
| EP | 0370810 | * 5/1990 | ........... B01F/17/00 |
| WO | WO 97/46223 | * 12/1997 | ........... A61K/9/127 |
| WO | WO 98/27209 | * 6/1998 | ........... C12N/15/12 |
| WO | WO 01/07486 | 2/2001 | |

OTHER PUBLICATIONS

Byk & Scherman *Exp. Opin. Ther.* 8(9): 1125–1141 (1998).
Domb, et al., "Polymers in gene therapy," in *Frontiers in Biological Polymer Applications* (Ottenbrite, ed.) Technomic: Lancaster, vol. 2, pp. 1–16 (1999).
Kiely, et al., "Hydroxylated nylons based on unprotected esterified D–glucaric acid by simple condensation reactions," *J. Am. Chem. Soc.* 116: 571–578 (1994).
Ledley, "Nonviral gene therapy: The promise of genes as pharmaceutical products," *Human Gene Therapy* 6: 1129–1144 (1995).
Lee, et al., "Self aggregates of hydrophobically modified chitosan for DNA delivery," *Proceed Intl. Symp. Control. Rel. Boiact. Matter* 24:651–652 (1997).
Mao, et al., "DNA–chitosan nanospheres: derivitization and storage stability," *Proc. Intl. Symp. Control Rel. Bioact. Matter* 24: 671–672 (1997).
Richardson, et al., "Evaluation of highly purified chitosan as a potential gene delivery vector," *Proceed Intl. Symp. Control Rel. Bioact. Matter* 24: 649–650 (1997).
Takakura, et al., "Control of pharmaceutical properties of soybean tyrosine inhibitor by conjugation with dextran 1: synthesis and characterization," *J. Pharm. Sci.* 78(2):117–121 (1999).
Treco & Selden, "Non viral gene therapy," *Molec. Med. Today* 1(7):299–348 (1995).
Walsh, et al., "Combination of drug and gene delivery by gelatin nanospheres for the treatment of cystic fibrosis," *Proc. Sym. Control. Rel. Bioact. Mater.* 24: 75–76 (1997).
Yamaoka, et al., "Effect of cation content of polycation–type gene carries on in vitro gene transfer," *Chemistry Letters*, 1171–1172 (1998).

* cited by examiner

*Primary Examiner*—James O. Wilson
*Assistant Examiner*—Ganapathy Krishnan
(74) *Attorney, Agent, or Firm*—Pabst Patent Group LLP

(57) ABSTRACT

The invention provides a polycation composition comprising a polysaccharide chain having an amount of saccharide units ranging from 2 to 2000, at least one oligoamine directly grafted to said polysaccharide chain per each segment of 5 saccharide units, wherein said oligoamine is selected from the group consisting of a linear, branched and cyclic alkyl amine having at least two amino groups, and at least one further grafted group selected from the group consisting of a hydrophobic and an amphiphilic group directly grafted to said polysaccharide chain per each segment of 50 saccharide units, wherein said hydrophobic or amphiphilic group includes an aliphatic chain of at least 4 carbons atoms.

26 Claims, No Drawings

CATIONIC POLYSACCHARIDE COMPOSITIONS

The present invention relates to a biodegradable polycation composition as well as to a biodegradable polycation complex of said composition together with a polyanion.

More specifically, the present application is directed to cationic polysaccharide derivatives made from the conjugation of oligoamines onto a polysacchide chain wherein said oligoamine conjugated polysaccharide further comprises hydrophobic or amphiphilic groups along the polymer chain. The oligoamines having at least two amino groups are conjugated with at least one oligomer per five saccharide units. The hydrophobic groups including saturated and unsaturated hydrocarbons derived from for example natural and synthetic fatty acids; cholesterol derivatives, aromatic groups such as naphthyl and benzyl groups, and the like. The hydrophobic and amphiphilic groups are positioned with at least one group per 50 saccharide units.

Gene therapy is a process by which genes are introduced into cells which then become mini-factories which manufacture and release essential compounds in cells and tissue which improve the life of the patient. Gene therapy has the potential to revolutionize the treatment of genetic disorders, diseases associated with a genetic component like cancer, AIDS, and many other diseases. Gene therapy may be the only remedy for some individuals who would otherwise die or be severely disabled. Gene transfer may also be employed for systemic protein and peptide-like hormone administration. Nucleic acid sequences coding for a protein (insulin, growth hormone) would be administered to the patient allowing endogenous production of their own medication.

Successful gene therapy requires the identification of an appropriate therapeutic gene for treatment of the disease, in addition to a delivery system by which that gene can be delivered to desired cell type both efficiently and accurately. Early attempts of gene transfer involved the removal of cells from the individual, and the alteration of the cells in the culture by the introduction of a functioning copy of the gene. The next step included grafting the genetically engineered cells back into the patient. This ex vivo approach to gene therapy is obviously limited to those target tissues that are not undergoing frequent multiplication and cell generation that could cause progressing elimination of the grafted cells. The ability of the altered cells to efficiently recombine with the target tissue is another limiting factor of the ex vivo approach since many cells do not exhibit the ability to recombine.

The limitation and the complexity of the ex-vivo approach facilitated the development of direct in vivo gene transfer methods. Direct gene therapy involves the administration of the gene into the body, targeting of the gene to the desired cells and into the nucleus of said genes, and expression of functioning gene products therein. Currently there are two different approaches for direct gene transfer. One is a viral approach and the other is a non-viral approach. Viral and non-viral gene therapies differ in the methods used to deliver genes to the target cells and direct the uptake of gene into the nucleus. Viral gene therapies employ genetically engineered viral particles to deliver the gene to target cell, and non-viral gene therapies employ gene delivery systems comprised of synthetic or semi-synthetic gene formulations. The limitations of viral therapies relate to the residual viral elements within the viral vectors which can be immunogenic cytopathic, or recombinogenic.

Antisense technology has introduced the possibility of down-regulating or specifically turning off the expression of individual genes. This technology has enormous therapeutic potential. Antisense oligodeoxynucleotides (AON or ODN) constitute sequences of 15 to 21 nucleotides with the order of the nucleotides providing the molecule with the specificity to target genetic material. An oligonucleotide whose bases are tailored to complement part of a particular mRNA, can bind to and complex with that section of the mRNA. This can prevent gene expression which may prevent protein synthesis by passive or reactive inhibition of mRNA translation. Antisense ODN's to DNA seem to inhibit DNA transcription by formation of a triple helix.

Antisense oligonucleotides enter cells by pinocytosis and/or receptor-mediated endocytosis after binding to cell surface antigens. Uncharged oligomers enter cells by passive diffusion and charged oligomers enter by endocytosis. It seems that oligomers are not internalized by cells very efficiently. Methods for improving cellular uptake and biological efficacy of ODN's have been devised, including their conjugation to a synthetic polypeptide poly(L-lysine) tail with or without transferrin, or encapsulation in cationic or antibody—targeted liposomes.

As with other modes of contemporary gene therapy, delivery remains a central and crucial issue. For example, Antisense oligonucleotides per se are thought not to cross the intact Blood Brain Barrier (BBB). There are no studies analyzing the passage of antisense oligomers across the Blood Brain Barrier. Attempts to deliver them across the BBB by hyperosmotic BBB disruption after conjugation or by incorporation into liposomes have, as a whole, been unsuccessful. Direct injection of free antisense results in their rapid breakdown.

Although, most research in vivo gene therapy has focused on the use of recombinant virus vectors, progress has been made toward developing non-viral formulations of gene for in vivo human gene therapy. The advantages of non-viral vectors are that they can introduce DNA into non-dividing cells, do not integrate into the chromosome, do not posses infective risk, and are potentially less expansive than viral vectors. The principle underlying non-viral gene delivery is that the problem of delivering DNA in vivo is not significantly different from the problem of delivering conventional drugs or biological products to intracellular compartment in the body. Non-viral gene therapies involve known drug delivery methods for the administration and targeting of genes to selected cells in vivo, where they express therapeutic products.

Various methods have been described for non-viral gene therapy, ranging from the direct administration of "naked" plasmid DNA to the systemic administration of complex synthetic formulations. Some approaches are aimed at developing "artificial viruses" that attempt to mimic the process of viral infection using synthetic or semi-synthetic components. Others apply the theory and method of advanced, particulate drug delivery to administer DNA to selected somatic targets. These approaches employ plasmid DNA complexes containing lipids, proteins, peptides, or polymeric carriers. The principle disadvantage associated with non-viral systems has been insufficient levels of gene expression, irreproducibility and significant variations in gene expression on various cell types.

The two classes of synthetic gene delivery systems that have been investigated most actively involve the use of either cationic liposomes or polycationic polymers. The assembly of these systems is achieved by an electrostatic condensation of the "anionic" DNA with the "cationic" moiety of either a lipid or a synthetic polymer. The cationic polymer-based systems have been most widely associated with the formulation of receptor-mediated gene delivery systems. This technique employs the ability of receptors on the surface of a variety of different cells to efficiently bind and internalize a ligand. Several ligands have been exploited for the efficient internalization of DNA-ligands complexes. These include: asialoorosmucoid and other galactosylated proteins which target the hepatic asialoglycoprotein receptor; transferrin which binds to the transferrin receptor and mannosyl which is recognized by the mannose receptor of macrophages. Targeting ligands are covalently linked to a polycation polymer, typically to poly(lysine) derivatives, and then form a ligand-poly(lysine)-DNA complex by the ionic interaction between the positively charged poly(lysine) and the negatively charged DNA. Often, an endosomolytic agent is added to the transfection mixture to induce endosomal lysis and enhance DNA release from the endosome in order to achieve high transfection efficiency. The efficiency of poly(lysine)-DNA conjugates in transfecting numerous cell types in vitro has been demonstrated, but their potential usefulness for in vivo human gene therapy is limited due to their cytotoxicity.

More advanced polymeric gene delivery systems employ macromolecules with a very high cationic charge density that act as an endosomal buffering system, thus suppressing the endosomal enzymes activity and protecting the DNA from degradation. The high cationic charge density mediates both DNA condensing and buffering capacity, that diminish the requirement for an endosomolytic agent addition.

Polymers used in Gene Transfer

The polycations used for gene complexation are polyamines that become cationic at physiologic conditions All polymers contain either primary, secondary, tertiary or quaternary amino groups capable of forming electrostatic complexes with DNA under physiologic conditions. The highest transfection activity is obtained at a 1.1–1.5 ratio of polycation to DNA. The most studied polyamines for gene transfer includes, poly(lysine) and its derivatives, polyamidoamine starburst dendrimers, polyethyleneimine, natural and modified polysaccharides, and acrylic cationic polymers. The details for each polymer class are described in Domb et al. (A. Domb, M. Levy, Polymers in gene therapy, Frontiers in Biological Polymer Applications, R. M. Ottenbrite (ed), Technomic, Vol. 2, 1999, 1–16.).

Polycations may be more versatile for use than the liposomes and other conventionally used spherical gene carriers. Several polycations have been reported to induce gene expression for example diethylaminoethyl dextran and other cationized polysaccharides [F. D. Ledley, Huiman Gene Therapy, 6, 1129, 1995; Yamaoka et al. Chemistry Letters, 1171–72, 1998]. These polymers have little structural similarity with each other except possessing cationic groups.

Cationic polysaccharides have been used for gene delivery. Chitosan, a linear cationic polysaccharide was suggested by several authors for gene delivery [K. W. Leong et al, DNA-Chitosan nanospheres: Transfection efficiency and cellular uptake, Proceed. Intl. Symp. Control. Rel. Bioact. Mater. 24:75–76, 651–652, 671–674, 1997; R. Richardson, H. V. J. Kolbe, R. Buncan, Evaluation of highly purified chitosan as a potential gene delivery vector, Proceed. Intl. Symp. Control. Rel. Bioact. Mater. 24:649–650, 1997] DNA-chitosan nanospheres were found to be significantly less toxic than poly(L-lysine) or Lipofectin using the MTT test. Compared to standard Lipofectamine mediated gene transfer, these nanospheres yield lower levels of gene expression in HEK 293 (human embryonic kidney cells), IB3 (bronchial epithelial cells) and HTE (human tracheal epithelial cells). Surface modification of DNA/chitosan complex nanoparticles by covalently binding poly(ethylene glycol), transferrin and mannose-6-phosphate receptor to facilitate entry into cells and improve storage stability was also studied. The Purified and hydrophobized chitosan has also been suggested as carrier for genes [K. Y. Lee, I. C. Kwon, Y. H. Kim, W. H. Jo, S. Y. Jeong, Selfaggregates of hydrophobically modified chitosan for DNA delivery, Proceed. Intl. Symp. Control. Rel. Bioact. Mater. 24–651–652, 1997].

Midox (WO 95/30020) describes a polypeptide such as polylysine modified at the g-amino group with a molecule bearing hydroxyl groups. Genzyme describes in WO 97/462 lipid derivatives of short chain alkylamines such as spermine and spermidine for use in gene transfection. For example one or two spermine or spermidine groups attached to cholesterol via an amide or carbamate bonds. WO 98/27209 to Emory Univ. describe a range of modified cationic polypeptides based on lysine for use in gene transfection.

The polymers described in the prior art can be grouped into two catagories: One including linear or dendrimeric polymers with random distribution of amino groups which are part of the polymer backbone such as poly(ethylene imines), poly(amido-amine) dendrimers, and poly (alkylamino-glucaramide). The second including linear polymers with a single primary secondary or tertiary amino group attached to the polymer units. Examples of such polymers are: poly(dimethylaminoethyl methacrylates), dimethylamino dextran, and polylysines.

All of the above polymers are polycations with a random distribution of the cationic sites. This randomness is probably the reason for the fact that these polymers may work for some nucleotides and cell types and not for others. Most of these polymers are toxic to cells and non-biodegradable, while the polymers based on amino acids such as polylysines are immunogenic.

It can be said that in the prior art, little attention was given to:
1. the structure of the polycation, the charge density and space distribution of cationic groups in the polymer to optimize complexation with anionic nucleotides;
2. the type of cationic groups, primary, secondary or tertiary groups were considered as cationic sites.
3. the toxicity and immunogenicity of the polymer;
4. the biodegradability and elimination properties of the polymer carrier;

In general, it has been believed that the cationic charge of the polymers is the main factor important for complexation and transfection. Also, these cationic polymers did not result in high enough transfection yield for commercial interest in ex-vivo experiments, in addition to animal experimentation. The degradation and elimination of the polymer carrier was not carefully treated and most polycations described for use in gene therapy are not biodegradable and/or toxic.

In designing a universal polycation system for gene delivery one should consider the way in which a plasmid becomes active in the cell and tissue. The plasmid has first to be protected from DNA degrading enzymes in the extracellular medium, then penetrate the cell wall, protected from degrading systems, i.e. the lisosome and enzymes, in the intracellular medium until it is internalized in the nucleus, penetrate into the nucleus and being released in its active form from the polymer carrier.

This invention describes a versatile and universal polycation system based on oligoamine grafted on natural or synthetic polysaccharides that is capable of complexing various plasmids and antisense, administering them into various cells in high yields and into the nucleus in active form to produce the desired protein.

It is the objective of the present invention to provide polycations that:
1. better fit the complexation requirements for effective delivery of a plasmid or an antisense;
2. biodegrade into non-toxic fragments at a controlled rate;
3. non-toxic and no-immunogenic in vivo;
4. form a stable enough complex with low and high molecular weight polynucleotides including therapeutic plasmids and antisense.
5. provide effective polymeric delivery system that result in a high transfection yield in a range of cells and in tissues.
6. can be reproducibly prepared at an affordable cost.

Another objective of this invention is to provide a controlled release of DNA in tissue or cell by complexing DNA with designed polymers that gradually de-complex and release the DNA or by incorporation of the complexed polynucleotides in a biodegradable matrix which will release the DNA in the site of insertion for periods of weeks and months.

Thus, according to the present invention there is a polycation composition comprising:
a) a polysaccharide chain having an amount of saccharide units ranging from 2 to 2000;
b) at least one oligoamine directly grafted to said polysaccharide chain per each segment of 5 saccharide units, wherein said oligoamine is selected from the group consisting of a linear, branched and cyclic alkyl amine having at least two amino groups; and
c) at least one further grafted group selected from the group consisting of a hydrophobic and an amphiphilic group directly grafted to said polysaccharide chain per each segment of 50 saccharide units, wherein said hydrophobic or amphiphilic group includes an aliphatic chain of at least 4 carbons atoms.

In another aspect of the present invention, there is provided a biodegradable polycation complex with a polyanion comprising:
a) a polysaccharide chain having an amount of saccharide units ranging from 2 to 2000;
b) at least one grafted oligoamine per 5 saccharide units, wherein said oligoamine is selected from the group consisting of a linear, branched and cyclic alkyl amine having at least two amino groups; and
c) at least one grafted hydrophobic or amphiphilic group per 50 saccharide units, wherein said hydrophobic or amphiphilic group includes an aliphatic chain of at least 4 carbons atoms; complexed with
d) an anionic macromolecule selected from the group consisting of polynucleic acids, proteins and polysaccharides that are anionic.

In especially preferred embodiments of the present invention, said polycation has a structure selected from the group consisting of a comb-like chain, a branched chain and a cross-linked chain.

In a preferred embodiment of the present invention said anionic macromolecule is selected from the group consisting of a plasmid, an open chain polynucleic acid, an oligonucleotide, an antisense, a peptide, a protein, an anionic polysacharide e.g. heparins and combinations thereof.

In another preferred embodiment of the present invention said polysaccharide chain is selected from the group consisting of dextrans, arabinogalactan, pullulan, cellulose, cellobios, inulin, chitosan, alginates and hyaluronic acid.

In a further preferred embodiment of the present invention said saccharide units are connected by a bond selected from the group consisting of acetal, hemiacetal, ketal, orthoester, amide, ester, carbonate and carbamate.

In an even further preferred embodiment of the present invention said polysaccharide is a synthetic polysaccharide formed from the condensation of an aldaric acid and a diaminoalkane.

In a preferred embodiment of the present invention said grafted oligoamine is grafted to said polysaccharide chain by a bond selected from the group consisting of amine, amide and carbamate. In another preferred embodiment, the oligoamine has the formula:

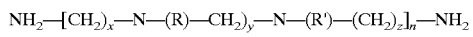

$$NH_2-[(CH_2)_x-N-(R)-CH_2)_y-N-(R')-(CH_2)_z]_n-NH_2$$

wherein x, y, z are an integer between 0 and 4 and x+y+z is between 1 and 4 and n is at least 1 when x+y+z=2 or more, or at least 2 when x+y+z=1 and wherein R and R' groups are H or an aliphatic side group of 1 to 6 carbons.

In an especially preferred embodiment of the present invention, said oligoamine is a peptide of up to 20 amino acids wherein at least 50% of the amino acids are cationic including lysine, ornithine and arginine.

In a further preferred embodiment of the present invention said oligoamine is selected from the group consisting of spermine and derivatives thereof.

In an even further preferred embodiment of the present invention said oligoamine is selected from the group consisting of a linear and branched ethyleneimine oligomer having up to 10 ethylene imine units.

In an even further preferred embodiment of the present invention said oligoamine is selected from the group consisting of a a peptide consisting of up to 20 amino acids with at least 50% contain a cationic side group including, lysine, ornithine, and diphthamic acid.

In a preferred embodiment of the present invention said amphiphilic residue is selected from the group consisting of fatty chains, phospholipids, cholesterol derivatives, ethylene glycol oligomers and propylene glycol oligomers, wherein said ethylene and propylene glycol oligomers have a fatty chain block on one side.

In a further preferred embodiment of the present invention said amphiphilic residue is connected to said polysaccharide chain by a bond selected from the group consisting of an amine, amide, imine, ester, ether, urea, carbamate and carbonate.

In an even further preferred embodiment of the present invention said amphiphilic residue facilitates the crossing of the polycation through biological membranes.

In a preferred embodiment of the present invention said polycation composition is not toxic or immunogenic.

In an even further preferred embodiment, the composition of the invention further comprises a ligand for facilitating the binding of said composition to a predetermined type of cell or tissue.

In further preferred embodiments of the present invention, there is provided a biodegradable polycation composition as hereinbefore defined in combination with cationic and nonionic lipids or in combination with polymers for enhanced cell transfection.

The invention further provides a pharmaceutical composition comprising a polycation composition as described above, in combination with a pharmaceutically acceptable carrier, said composition being prepared by methods known per se utilizing standard pharmaceutically acceptable carriers as is known in the art.

In a preferred embodiment of the present invention said biodegradable polycation composition can be used as a scaffold for cell growth.

Furtheremore said composition can be used for non-medical applications such as to provide cationic coating in the printing and electronic industry.

The invention also provides a pharmaceutical composition comprising the composition described above, in combination with amphiphilic cationic and/or nonionic lipids and cationic and nonionic polymers generally used for nucleotide delivery. Examples of lipids include DOTMA, DOTAP, DMRIE, GAP-DLRIE, DODHF, aklylated spermine, and other derivatives described in: G. Byk and D. Scherman, Exp. Opin. Ther. (1998) 8(9):1125–1141; D. A. Treco and R. F. Selden, non viral gene therapy, Molec. Med. Today, 1995, 1(7):299–348)

The present invention provides a range of biodegradable polycations based on grafted oligoamine residues on synthetic or a natural polysaccharides which are effective in delivering plasmids and antisense for a high biological effect. The grafting concept where side chain oligomers are attached to either a linear or branched hydrophilic polysaccharide backbone, allows two/three dimensional interaction with an anionic surface area typical to the double or single strand DNA chain. This type of flexible cationic area coverage is not available with non-grafted polycations or low molecular weight cations. Low molecular weight amines and their lipid derivatives such as the lipofectin and lipofectamine have a localized effect on the DNA which the degree of complexation is dependent on how these small molecules organized around the anionic DNA. Each molecule has to be synchronized with the other molecules at all times of the transfection process whereas when the oligoamines are grafted on a polymer they are already synchronized and each side chain helps the other side chains to be arranged to fit the anionic surface of the given DNA. By grafting the functional groups is an average distribution along a polymer chain at a certain distance between each other (for example, grafting an oligoamine chain every one, two, three or four polymer unit may provide optimal complexation with various DNAs.

The use of biodegradable cationic polyol carriers is especially suitable for transfection and biological applications because they are water soluble and miscible in aqueous vehicles. The resultant grafted polymers are water soluble or dispersible in water, it can be readily transported to cells in vivo by known biological processes, and acts as an effective vehicle for transporting agents complexed with it.

The compositions of the present invention are composed of a natural or synthetic polysaccharide backbone with a grafted complexation functionality, i.e. aliphatic organic cationic residues containing at least two amino groups. The alkyl amino cationic residues are distributed in an optimal charge distribution tailored for as many plasmid or oligonucleotide for optimal transfection results. The polymer has hydrophobic/hydrophilic side groups that allow penetration of the polymer-plasmid complex into cells for transfection.

DETAILED DESCRIPTION OF THE INVENTION

The present invention provides a new class of non-viral polymeric vectors that can be used for both in vitro and in vivo transfer of biologically active molecules. In particular, these vectors can be used for gene transfer applications. The polycationic compositions of the present invention can achieve gene transfer efficiencies in vitro that are superior to commercially available cationic liposome preparations. Further, the low toxicity and lack of serum inhibition of the compositions is suitable for in vivo use. The present invention provides a vector that can achieve in vivo gene transfer efficiencies that compare favorably to viral vector systems. The present invention further provides a method to increase the capacity of solutions to carry complexes of nucleic acids and the polymeric vector without precipitation or toxic ionic effects on cells.

Furthermore, the unique polycationic structure of this class of polymers associates with many suitable bioactive molecules, including proteins and other compounds that possess multiple anionic sites. The polymer can act as a carrier to deliver the associated bioactive molecule, in vivo or in vitro, to the cells of interest for the bioactive molecule.

In addition, the unique polycationic structure of this class of polymers are biodegradable and readily eliminated from the body after administration.

In one aspect the invention provides a complex comprising a nucleic acid and a transfection agent, wherein:

i) the transfection agent is obtained by the conjugation of short aliphatic oligoamine to a polysaccharide containing hydrophobic and/or amphiphilic side groups to allow penetration into cells.

ii) the short aliphatic oligoamine conjugated to the polymer contains at least two amino groups.

iii) The hydrophobic and/or amphiphilic sites attached to the polymer are for example fatty chains, phospholipids or cholesterol derivatives or ethylene or propylene glycol oligomers with or without a fatty residue block, which have the capacity to allow penetration into cells. The density and quality of the hydrophobic side groups are selected to allow optimal transfection both in vitro (cells) and in vivo (humans).

iv) The transfection agent is able to deliver a gene, antisense or nucleic acids into cells and/or nucleus, release them in active from to allow substantial biological effect by the gene or antisense and, biodegrade into non-toxic fragments that are eliminated from the cell or the body.

As used herein the term "transfection agent" means any chemical agent capable of facilitating the entry of a nucleic acid into a eukaryotic cell.

As used herein the term "nucleic acid" means a polymer of nucleotides, and specifically includes plasmids, coding DNA sequences, mRNAs, and antisense RNA molecules. A nucleic acid can be single—or double—stranded. The nucleic acids can also contain one or more substitute linkages. These substitute linkages include conventional alternative linkages such as phosphorothioate and phosphoramidate, and are synthesized as described in generally available literature. Nucleic acids also include those nucleotides in which the sugar moiety has been modified by, for example, substitution of one or more hydroxyl groups with halogen, aliphatic groups, or functionalized as ethers, amines, or wherein the ribose or deoxyribose is replaced with other functionally equivalent structures. In particular, the sugar-phosphate backbone may be replaced with a non-carbohydrate backbone such as a peptide or other type of polymer.

As used herein the term "primary amine" means any amine that possesses one or more primary amine functionality.

As used herein the term "secondary amine" includes amine moieties having at least two pendent hydrocarbon groupings, and also includes, in the appropriate context, tertiary and quaternary amines.

As used herein "a" can mean one or more, depending upon the context in which it is used.

As used herein "aliphatic" and "aromatic hydrocarbons" include both substituted and unsubstituted compounds, wherein the substitution can occur in the backbone or pendent groupings of the hydrocarbon. Aliphatic compounds may be branched or straight chained.

As used herein "polysaccharide" means, linear, branched or crosslinked natural or chemically modified polysaccharides. It also includes synthetic copolymers having at least 40% saccharide units in the polymer backbone. A particular example is polyamides of glucaric acid with alkanediamines.

As used here "oligoamine" means a linear, cyclic and branched alkaneamine that contain at least two amino groups. The molecular weight of the oligoamine is limited to about 2,000 Daltons.

The present invention relates to a novel class of polycationic polysaccharides having effective nucleic acid transfection properties and bioactive agent delivery attributes. The polymers are obtained from the conjugation of an oligoamine to a polysaccharide chain. The polysaccharide carrier, the oligoamine and the grafting ratio bond type are selected to enhance the degree and efficiency of transfection. For example, polymers can be selected based upon the density and distribution of the cationic sites on the polymer to obtain transfection agents that are tailored to the anionic charge distribution of the nucleic acid being transfected, and the anionic charge distribution of the type cell being targeted. Various substituents can also be incorporated into the polymer to affect the properties of the polymer by improving the transfection efficiency thereof.

The present invention provides (1) a class of polycationic polymers, (2) a class of complexes comprising these polymers with nucleic acids, and (3) a class of complexes comprising these polymers with suitable anionically charged bioactive agents. The class of polycationic polymers comprises products obtained by the grafting of an oligoalkaneamine onto a suitable polysaccharide, wherein the grafted oligoamine contains at least Two amines. in a particularly preferred embodiment, the grafted primary amine has one primary amine and three secondary amines.

Examples of suitable polysaccharides include, for example, dextrans, arabinogalactan, pullulan, cellulose, chitosan, inuline, hyaluronic acid, and alginates having from 2 to 2,000 saccharide units. Other classes of polysaccharides are polyureas or polyamides of aldaric acids such as mucic acid, glucaric acid, galactaric acid, xylaric acid, and their various isomers polycondenced with aliphatic diamines. The copolymerization of the comonomers may be performed generally by methods known in the art, including by condensation reactions. Examples of suitable polycondensation techniques are described in detail in Kieley et al., *J. American Chemical Society*, 116, 571–578 (1994), Kieley et al., U.S. Pat. Nos. 3,225,012; 5,434,233; 5,312,967; 5,473,035; 5,833,230; and 5,329,044; and Dewar et al.

The ionic association of the polymer/nucleic acid charges neutralizes the anionic charges on the nucleic acid and allows the complex to interact and bind more favorably with the negatively charged cell surface. If an excess of cationic sites are present on the polymer, i.e. more than are necessary to neutralize the anionic charges on the nucleic acids, these excess cationic charges may facilitate the attraction of the complex to the ionically charged surface of the cell, thereby facilitating entry of the complex into the cell. The polymers may also compact the nucleic acids upon complexation, which further enhances the likelihood of entry.

Although the present invention is limited to grafted oligoalkylamines, various substitutents can be incorporated into the polymer carrier. For example, the hydroxyl groups on the aliphatic chain of the monosaccharides can be substituted with aliphatic hydrocarbons, amides, azo, carbamate, carboxylic esters, ethers, thioethers, thiols, fluorescent derivatives, and sulfonic acids. One is often able to increase the hydrophobicity of the polymer (where hydrophobicity is desired) by alkylating the secondary amines with long chain hydrocarbons. Alternatively, one may increase the amphiphilicity by attaching a polyethylene glycol (PEG) chain.

The structure of the polymer can also be altered, by known techniques, to optimize the transfection and delivery efficiency of the polymer for each cellular target on the basis of the physiological and biological characteristics of that target. For example, the efficiency of gene delivery to cells can be enhanced by the addition of peptides with the nuclear targeting signal of simian virus 40 to the polymer. Several protein ligands are also known that can be covalently coupled to the polymer and then incorporated into a ligand-nucleic acid complex. The resulting complexes retain their ability to interact specifically with cognate receptors on the target cell.

Another method for improving the efficiency of gene delivery is to enhance the release of DNA from the endosome after it has entered the cell. Adenoviral particles can be coupled to the polymer to increase this efficiency. Synthetic peptides can also be designed and incorporated into the polymer in order to enhance endosomal release.

The biodegradable polycation compositions of the present invention are of general use for gene transfer and bioactive agent delivery with respect both to cell type and size of nucleic acid or bioactive agent because the transfection is driven by ionic interactions. Any selected cell into which transfection of a nucleic acid or delivery of a bioactive agent (via transfection or other means) would be useful can be targeted by this method, by administering the composition in a suitable manner to bring the composition into contact with the selected cell, as is known in the art. Cells can be within a tissue or organ, for example, supplied by a blood vessel into which the composition is administered. The composition of the present invention can be formulated into a slab, pellet, microsphere and nanosphere made of a biodegradable component such as a biodegradable polymer or fat to allow targeting and/or controlling long term release of the gene complex to the blood system or to a specific site as known in the literature for common bioactive molecules. Alternatively, for example, the composition can be directly injected into the target tissue or organ. As a further example, the lungs can be targeted by inhalation or intratracheal injection of the complex or particles containing the complex. The invention has application to all eukaryotic cells; it can be used particularly for mammalian cells and subjects, such as humans, cows, horses, sheep, pigs, rats and mice. Some examples of cells that can be targeted by the composition of the present invention include fibroblasts, epithelial cells, endothelial cells, blood cells and tumor cells.

Due to the fact that the polyol backbone according to one of the embodiments of the invention is both biodegradable and regularly imported into living cells as part of normal biosynthetic processes, it is nontoxic and nonimmunogenic, which offers a distinct advantage over viral vectors when used as transfection agents. Similarly because polyols do not generally contain natural binding sites for serum, the polyol backbone is not negatively impacted by circulating serum proteins such as herparin and albumin. Complexes formed with the polymers thus reach targeted cells intact without significant serum inhibition, in contrast to polycationic lipids which are substantially impacted by natural systemic serums.

The amount of DNA that is carried in solution can also influence the degree of transfection of the composition. The concentration of DNA in solution is often limited by its tendency to precipitate at higher concentrations. In some applications, the DNA concentration in solution is limited to about 1.0 g/l. Increased amounts of DNA-polymer in solution which does not precipitate, may be achieved if proper methods of preparation and optimal polymer to DNA ratio and polymer structure are used. In such preparations it may be possible to obtain solutions carrying 20 grams of DNA per litter of solution.

Suitable delivery and transfection conditions are when the cell and composition temperature is between about 18° C. and about 42° C., with a preferred temperature being between about 22° C. and about 37° C. For administration to a cell in a subject, the complex, once in the subject, will of course adjust to the subject's body temperature. For ex vivo administration, the complex can be administered by any standard method that would maintain viability of the cells, such as by adding the complex to a culture medium (appropriate for the target cells) and adding this medium directly to the cells. The medium used in this method should be aqueous and non-toxic so as not to render the cells non-viable. In addition, the medium can contain nutrients for maintaining viability of cells, if desired.

The composition can be administered in vivo by parenteral administration, e.g., by intravenous injection including regional perfusion through a blood vessel supplying the tissue(s) or organ(s) having the target cell(s). Injectables can be prepared in conventional forms, such as liquid solutions, suspensions, or emulsions. A slow release or sustained release system can also be used, allowing the maintenance of a constant dosage level.

Other means of administration can include inhalation of an aerosol, subcutaneous, intraperitoneal or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods can include oral administration, particularly when the complex is encapsulated, or rectal administration, particularly when the complex is in suppository form.

A pharmaceutical composition according to the present invention can include the composition and a pharmaceutically acceptable carrier suitable for the selected mode of administration. A pharmaceutically acceptable carrier includes any material that will not cause any undesirable biological effects or interact in a deleterious manner with the biological host or with the components within the pharmaceutical composition. A pharmaceutical composition can further include other medicinal agents, pharmaceutical agents, adjuvant, diluents, stabilizers, etc., as long as they do not interfere with the action of the composition. Actual methods of preparing such dosage forms are known or will be apparent to those skilled in the art, (for example—Martin, E. W. *Remington's Pharmaceutical Sciences*, latest edition, Mack Publishing Co., Easton, Pa.)

Transfections using combinations of a plasmid:polycation complex of this invention and various cationic, anionic and amphiphilic polymers and molecules. the plasmid dna complex consisted of plasmid dna, oligoamine polysaccharide condensing agent and a peptide (a peptide described in U.S. patent application Ser. No. 07/913,669, filed Jul. 14, 1992). addition of amphipathic polymers: polyethylene glycol (PEG); polypropylene glycol (PPG) and PEG-PPG copolymers, phosphatidyl choline, cholesterol derivatives, and non-ionic surfactants, the transfection efficiency of the plasmid dna complex was significantly enhanced over the plasmid dna complex alone or the polymers alone. The addition of an anionic polymer or lipid may result in destabilization of the net positively charged plasmid dna complex by its negative charge and thus may better release the plasmid in the nucleus or in the other hand may de-complex the plasmid and the activity may be reduced. Several mechanisms of action of amphipathic polymers may account including: stabilization of plasmid dna complexes due to coating; increased cell membrane permeability, thereby allowing easier passage of the plasmid dna complex through the cell; membrane and/or volume exclusion, increasing the concentration of plasmid dna complexes at the cell surface.

Another objective of this invention is to provide a controlled release of biologically active dna in tissue or cell by complexing them with the polycations of this invention that gradually de-complex and release the biomacromolecule, DNA, antisense, and a protein or a polysaccharide (heparin) or by incorporation of the complex in a biodegradable matrix, which will release the DNA or DNA complex in the site of insertion for periods of weeks and months.

The following polymers, oils and surfactants may be suitable for use as compounds which enhance gene transfection and/or prolong the localized bioavailability of a nucleic acid: salts of hyaluronates; salts of alginates; heteropolysaccharides (pectins); poloxamers (pluronics); poloxamines (tetronics); polyethylene glycols; dextrans; polyvinylpyrrolidones; chitosans; polyvinylalcohols; propylene glycols; phosphatidylcholines (lecithins); xanthan gum, polyethylene glycol-polylactic-glycolic acid (PEG-PLA), polyethylene glycol-polyhydroxybutyric acid (PEG-PHB), fatty acid and alcohols and their esters, glycofurol, cremophors, and oil mixtures. These substances may be prepared as solutions, suspensions, gels, emulsions or microemulsions of a water/oil (w/o), water/oil/water (w/o/w), oil/water (o/w) or oil/water/oil (o/w/o) type. Oil suspensions of lyophilized nucleic acid, such as plasmid DNA may be utilized. Carriers for these oil suspensions include, but are not limited to, sesame oil, cottonseed oil, soybean oil, lecithins, tweens, spans and miglyols. by "solutions" is meant water soluble polymers and/or surfactants in solution with nucleic acids. By "suspensions" is meant water insoluble oils containing suspended nucleic acids. By "gels" is meant high viscosity polymers containing nucleic acids. By "emulsion" is meant a dispersed system containing at least two immiscible liquid phases. Emulsions usually have dispersed particles-in the 0.02 to 100 micron range. Nucleic acids in the water phase can be dispersed in oil to make a w/o emulsion. This w/o emulsion can be dispersed in a separate aqueous phase to yield a w/o/w emulsion. Alternatively, a suitable oil could be dispersed in an aqueous phase to form an o/w emulsion. A "microemulsion" has properties intermediate to micelles and emulsions and is characterized in that they are homogenous, transparent and thermodynamically stable. They form spontaneously when oil, water, surfactant and cosurfactant are mixed together. Typically, the diameter of the dispersed phase is 0.01 to 0.1 microns, usually of the w/o and o/w type.

The compounds which prolong the bioavailability of a nucleic acid may also interact or associate with the nucleic acid by intermolecular forces and/or valence bonds such as: van der waals forces, ion-dipole interactions, ion-induced dipole interactions, hydrogen bonds, or ionic bonds. These interactions may serve the following functions: (1) stereoselectively protect nucleic acids from nucleases by shielding; (2) facilitate the cellular uptake of nucleic acid by endocytosis. To achieve the desired effects set forth it is desirable, but not necessary, that the compounds which prolong the bioavailability of a nucleic acid have amphipathic properties; that is, have both hydrophilic and hydrophobic regions. The hydrophilic region of the compounds may associate with the largely ionic and hydrophilic regions of the nucleic acid, while the hydrophobic region of the compounds may act to retard diffusion of nucleic acid and to protect nucleic acid from nucleases. Additionally, the hydrophobic region may specifically interact with cell membranes, possibly facilitating endocytosis of the compound and thereby nucleic acid associated with the compound. This process may increase the pericellular concentration of nucleic acid. Agents which may have amphipathic properties and are generally regarded as being pharmaceutically acceptable are the following: methylcelluloses, hydroxypropylcelluloses, hydroxypropylmethylcelluloses; heteropolysaccharides (pectins); poloxamers (pluronics); poloxamines (tetronics); ethylene vinyl acetates; polyethylene glycols; polyvinylpyrrolidones; chitosans; polyvinylalcohols; polyvinylacetates; phosphatidylcholines (lecithins); propylene glycol; miglyols; polylactic acid; polyhydroxybutyric acid; xanthan gum. Also, copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of n-vinyl purine (or pyrimidine) derivatives and n-vinylpyrrolidone. Nucleic acids may be loaded into biodegradable hydrogels such as crosslinked polysaccharides, and PEG based gels by placing swellable hydrogel systems in nucleic acid or complex solutions. Swellable hydrogels include but are not limited to crosslinked oxidized arabinogalactan and dextran with a polyamine calcium-crosslinked alginate, poloxamines (tetronics) and poloxamers (pluronics).

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Synthesis of Polycations

Experimental Section

All solvents and reagents were the best commercial grade available and were used as received. A sage-metering pump (model-365) was used. NMR spectra were recorded on a Varian 300 MHz instrument using CDCl3, D2O or d6-DMSO as solvents. Values were recorded as (ppm) relative to internal standard (TMS). Molecular weights of starting polymers and conjugates were determined on GPC instrument (Spectra physics program) containing a pump, column (Shodex KB-804 or KB-803, Japan) and refractive index (RI) detector. Mw were determined using pullulan standards of known molecular weights. Eluent used were: 0.05M NaNO3 for uncharged polymers and 5% (w/v) sodium phosphate monobasic in 3% acetonitrile (pH=4.0) for the polycationic polymers.

Oxidation of Dextran

Dialdehyde Dextran (1) was obtained by reacting dextran (1, Mw=9.3 to 500 Kd) in water with potassium periodate at 1:1, 1:3 and 1:5 (KIO4:Saccharide units) molar ratio. The mixture was stirred at room temperature in the dark for 5 h until a clear solution was obtained. The resulting polyaldehyde derivatives were purified from iodate ($IO_3^-$) and unreacted periodate ions ($IO_4^-$) by DOWEX-1 anion exchange chromatography (acetate form), following an extensive dialysis against DDW (12,000 cut-off cellulose tubing) for 2 days. The purified polyaldehyde was then freeze-dried to obtain a white powder in 85% average yield. Aldehyde content of oxidized polymers were determined by the hydroxylamine hydrochloride method (table 1).

Aldehyde content was determined by the hydroxylamine hydrochloride method. Oxidation of pullulan, arabinogalactan, soluble cellulose, dextrin, and other polytsaccharides was performed using the above procedure. Oxidation degrees from 30 to about 60% of the saccharide units were obtained.

Dextran-Spermine Conjugate (2)

1.0 gr. of dialdehyde Dextran (Mw=29 Kd, 50% dialdehyde) dissolved in 100 ml DDW, was slowly added during 4 h (Sage metering pump) into a Spermine solution containing 1.25 gr. Spermine (1.0 equimolar to aldehyde) dissolved in 50 ml Borate buffer (0.1M Boric-acid, pH=11.0). The purpose of the slow addition was to minimize crosslinking of Spermine into the polyaldehyde chains. The mixture was stirred gently at room temperature for 24 h and 1.0 gr. of NaBH4 (10 molar excess to aldehyde) was added and stirring was continued at the same conditions for 48 h. Then, another portion of borohydride (1.0 gr.) was added and stirring was continued for another 24 h at room temperature. The resulting light-yellow solution was poured into a dialysis membrane (3.5K MWCO) and dialyzed against DDW (3×5L) at 4° C. changing the water every 8 h. The purified solution was filtered to remove insolubles, and freeze-dried.

The synthesis was repeated several times and reproducible results were obtained (table 2).

Yield: 0.5 gr. (~25%, w/w). % N=12.0±0.5% (elemental analysis) and 1.2–1.5 (mole amine per (g conjugate (TNBS).

Alternatively, the resulted polysaccharide derivatives were purified at each step by lyophilization and extraction of the low molecular weight components using ethanol:water mixtures, dimethylsulfoxide and other solvents and mixtures that dissolve the unwanted molecules without dissolving or affecting the polysaccharide. Another procedure for purification of the desired polysaccharide, either after oxidation or after conjugation of the oligoamine, or after reduction with sodium borohydride, is by precipitation in a water miscible anti-solvent that dissolves the low molecular weight molecules (i.e unreacted reagent or reaction by-products) but precipitate the polymer. Usually, for an efficient purification the reaction solution is concentrated to minimize the amount of anti-solvent needed for effective precipitation. Suitable solvents include ethanol, propanols, and butanols. Oxidizing agents may include sodium periodate, osmium tetraoxide, permanganate, chromates and the like. Reducing agents such as sodium cyanoborohydride and borane-amine complexes can be used.

Synthesis of Cholesteric Acid N-hydroxy Succinimide Ester (3)

To 0.5 gr. of Cholesteryl chloroformate (1.12 mmole) dissolved in 25.0 ml of anhydrous THF, was added 0.4 ml of anhydrous DIEA (2.5 eq.). The mixture was cooled to 0° C. and 200.0 mg of solid N-hydroxy succinimide (1.5 eq.) were added and stirring was continued for 2 h at 0° C. and over-night at room temperature. Solvent was removed under reduced pressure and the crude was redissolved in 50.0 ml of diethyl-ether. Then, the ethereal solution was washed with DDW (2×20 ml) and brine (2×20 ml), dried over anhydrous $MgSO_4$, filtered and evaporated to dryness. The crude was crystallized in DCM:MeOH (1:5), stored at −20° C. for 24 h, filtered and dried in vacuum over P2O5.

Yield=0.5 g. (~85%). Rf (SiO2, 1% MeOH in DCM)= 0.65.

1H-NMR ($CDCl_3$): 5.422 (d, 1H, vinyl hydrogen of Chol), 4.597 (m, 1H, hydrogen bearing substituted hydroxyl of Chol), 2.828 (s, 4H, —CH2CH2- of NHS group), 2.045 (m, 2H), 1.006 (s, 3H), 0.915 (s, 3H), 0.873 (s, 3H), 0.869 (s, 3H) and 0.675 ppm (s, 3H).

Synthesis of Oleic Acid (cis-9-octadecenoic acid) N-hydroxy Succinimide Ester (4)

1.33 gr. of N-hydroxy succinimide (11.56 mmole, 1.5 eq.) and DIEA (1.35 ml), were dissolved in 50.0 ml of anhydrous THF and gently stirred at 0° C. under nitrogen atmosphere. Then, Oleoyl chloride (3.0 ml, 85% tech., 7.8 mmole, 1.0 eq.) dissolved in 50 ml of anhydrous THF was added dropwise during 1 h. The mixture was gently stirred for 2 h at 0° C. and over-night at room temperature. The resulting precipitate were discarded by filtration and the filtrate was evaporated under reduced pressure, redissolved in small amount of DCM and purified over silica-gel column using DCM as eluent. Fractions containing the product were combined and solvent was removed under reduced pressure. The resulting white solid was dried in vacuum over NaOH-pellets.

Yield=2.733 gr. (~92%).

$^1$H-NMR($CDCl_3$):0.874(3H, t, C$\underline{H}_3$CH$_2$(CH$_2$)$_5$—CH$_2$—CH=CH—CH$_2$(CH$_2$)$_5$—CH$_2$CO—NHS), 1.38 (20H, m, CH$_3$CH$_2$(C$\underline{H}_2$)$_5$—CH$_2$—CH=CH—CH$_2$(C$\underline{H}_2$)$_5$—CH$_2$CO—NHS), 1.74 (2H, m, CH$_3$C$\underline{H}_2$(CH$_2$)$_5$—CH$_2$—CH=CH—CH$_2$(CH$_2$)$_5$—CH$_2$CO—NHS), 2.004 (4H, m, CH$_3$CH$_2$(CH$_2$)$_5$—C$\underline{H}_2$—CH=CH—C$\underline{H}_2$(CH$_2$)$_5$—CH$_2$CO—NHS), 2.594 (2H, t, CH$_3$CH$_2$(C$_2$)$_5$—CH$_2$—CH=CH—CH$_2$(CH$_2$)$_5$—C$\underline{H}_2$CO—NHS), 2.83 (4H, s, NHS hydrogens) and 5.34 ppm (2H, m, CH$_3$CH$_2$(CH$_2$)$_5$—CH$_2$—C$\underline{H}$=C$\underline{H}$—CH$_2$(CH$_2$)$_5$—CH$_2$CO—NHS).

N-hydroxy succinimide derivatives of pivalic acid (C5-branched, 5), Hexanoic acid (C6-Linear, 6), Octanoic acid (C8-Linear, 7), Myristic acid (C14-Linear, 9) were prepared similarly.

Synthesis of Lauric Acid N-hydroxy Succinimide (C12-Linear, 8)

It was prepared exactly in a similar way as in the preparation of oleic acid N-hydroxy succinimide. In brief, 1.33 gr. of N-hydroxy succinimide (11.56 mmole, 1.5 eq.) and DIEA (1.35 ml) were dissolved in 50.0 ml of anhydrous THF and gently stirred at 0° C. under nitrogen atmosphere. Then, Lauroyl chloride (1.8 ml, 99% Sigma, 7.8 mmole, 1.0 eq.) dissolved in 50 ml of anhydrous THF was added dropwise during 1 h. The mixture was gently stirred for 2 h at 0° C. and over-night at room temperature. The resulting precipitate were discarded by filtration and the filtrate was evaporated under reduced pressure, redissolved in small amount of DCM and purified over silica-gel column using DCM as eluent. Fractions containing the product were combined and solvent was removed under reduced pressure. The resulting white solid was dried in vacuum over NaOH-pellets.

$^1$H-NMR ($CDCl_3$): 0.875 (3, t, C$\underline{H}_3$(CH$_2$)$_9$ CH$_2$CH$_2$CO—NHS), 1.214–1.435 (18H, m, CH$_3$(C$\underline{H}_2$)$_9$ CH$_2$CH$_2$CO—NHS), 1.736 (2H, m, CH$_3$(CH$_2$)$_9$C$\underline{H}_2$CH$_2$CO—NHS), 2.594 (2H, t, CH$_3$(CH$_2$)$_9$CH$_2$C$\underline{H}_2$CO—NHS) and 2.827 ppm (4H, s, NHS hydrogens).

Synthesis of Stearic Acid N-hydroxy Succinimide (C18-Linear, 10)

1.33 g. of N-hydroxy succinimide (11.56 mmole) and DIEA (1.5 ml, 8.62 mmole) were dissolved in 50 ml of anhydrous THF and gently stirred at 0° C. under nitrogen atmosphere. To this were added dropwise and during 1 h a solution of stearoyl chloride (2.35 g, 7.7 mmole) in 50 ml of anhydrous THF. After, the mixture was stirred at 0° C. for 2 h and overnight at room temperature. Solvent was removed under reduced pressure and the remaining white solid was redissolved in 200 ml of DCM. The organic phase were washed with DDW (2×100 ml), dried over anhydrous $MgSO_4$, filtered and evaporated to dryness. The reaming solid was dissolved in 100 ml of ethyl acetate and 200 ml of hexane and kept at −20° C. overnight. The resulting white crystals were collected by filtration and dried in vacuum over NaOH-pellets. The crystallized product was free from unreacted acid chloride as determined by $^1$H-NMR. The remaining filtrate was also evaporated to yield the product contaminated with 10% of the starting acid as determined by $^1$H-NMR.

$^1$H-NMR of crystallized product ($CDCl_3$): 0.867 (3H, t, C$\underline{H}_3$(CH$_2$)$_{14}$CH$_2$CH$_2$CO—NHS), 1.234–1.453 (28H, m, CH$_3$(C$\underline{H}_2$)$_{14}$CH$_2$CH$_2$CO—NHS), 1.735 (2H, m, CH$_3$(CH$_2$)$_{14}$C$\underline{H}_2$CH$_2$CO—NHS), 2.589 (2H, t, CH$_3$(CH$_2$)$_{14}$CH$_2$C$\underline{H}_2$CO—NHS) and 2.828 (4H, s, NHS hydrogens).

N-hydroxy succinimide derivatives of pivalic acid (C5-branched, 5), Hexanoic acid (C6-Linear, 6), Octanoic acid (C8-Linear, 7), Myristic acid (C14-Linear, 9)_Linoleic acid (cis,cis-9,12-octadecedienoic acid) (11), and Linolenic acid (cis,cis,cis-9,12,15-octadecatrienoic acid) (12) were prepared similarly.

Synthesis of di-Chol-L-Lysine-NHS (13)

Synthesis of di-Chol-L-Lysine-OMe 0.122 gr. of L-Lysine monomethyl ester ($5.05 \times 10^{-4}$ mole) was dispersed in 100 ml of anhydrous DMF under nitrogen atmosphere. To this mixture was added 0.7 ml of anhydrous TEA (4.5 eq.) and the mixture was cooled to 0° C. using ice bath. Then, 0.5 gr. of Cholesteryl chloroformate (2.2 eq.) was added and stirring was continued for 2 h at 0° C. and over-night at ROOM TEMPERATURE. The mixture was diluted with DDW (30.0 ml) and the product was extracted with diethyl ether (4×50 ml). The ethereal extracts were combined and washed with brine (2×50 ml), dried over anhydrous $MgSO_4$, filtered and evaporated to dryness. The crude product was purified by column chromatography over silica gel using DCM as eluent.

Yield=380 mg (~75%).

$^1$H-NMR ($CDCl_3$): 5.371 (d, 2H, vinyl hydrogen of Chol×2); 4.757 (m, 2H, MeOCOCH (C$\underline{H}_2$CH$_2$CH$_2$CH$_2$NHChol)NHChol), 4.523 (m, 4H, MeO-COCH (CH$_2$C$\underline{H}_2$C$\underline{H}_2$CH$_2$NHChol)NHChol), 4.316 (m, 2H, MeOCO—CH (CH$_2$CH$_2$CH$_2$C$\underline{H}_2$—NHChol)NHChol), 3.736 (s, 3H, methyl ester group), 3.154 (m, 2H, hydrogen bearing substituted hydroxyl of Chol×2), 2.295 (m, 4H, ×2 Chol), 1.003 (s, 6H, ×2 Chol), 0.92 (s, 6H, ×2 Chol), 0.871

(s, 6H, ×2 Chol), 0.849 (s, 6H, ×2 Chol) and 0.671 (s, 6H, ×2 Chol) ppm.

Removal of the Monomethyl Ester Group 200.0 mg of di-Chol-L-Lysine-OMe (0.2 mmole) were dissolved in 5.0 ml of THF. To this was added 3.0 ml of 1N NaOH aqueous solution (5 fold molar excess) and the mixture was stirred over-night at ROOM TEMPERATURE. Then, pH was adjusted to 1.0 using 1M aqueous HCl and THF was removed under a stream of nitrogen. The resulting white suspension was extracted with diethyl ether (3×20 ml), dried over anhydrous $MgSO_4$ and evaporated to dryness, The crude was crystallized in DCM:MeOH (1:5), stored at −20° C. for 24 h, filtered and dried in vacuum over $P_2O_5$.

Yield=180.0 mg (~95%).

$^1$H-NMR ($CDCl_3$) showed a full removal of the methyl ester-protecting group.

Synthesis of di-Chol-L-Lysine-NHS 150.0 mg of 5 (0.158 mmole), 5.0 mg of HOBT (0.2 eq.) and 70.0 μl of DIEA (2.5 eq.) were dissolved in 10.0 ml of anhydrous DCM. The mixture was cooled to 0° C. and 60.0 mg of EDC (2.0 eq.) were added and stirring was continued for 2 h at 0° C. and over-night at room temperature. The mixture was diluted with DCM (15 ml) and washed with DDW and brine (2×5 ml, each), dried over anhydrous $MgSO_4$, filtered and evaporated to dryness. The crude product was purified by column chromatography over silica-gel using DCM as eluent Yield=120.0 mg (~73%). The stracture was confirmed by $^1$H-NMR.

Synthesis of di-Oleate-L-Lysine-NHS (14)

Di-Oleate-L-Lysine-NHS was prepared in a similar manner to di-Chol-L-Lysine-NHS.

Yield: 76%, The stracture was confirmed by $^1$H-NMR.

Hydrophobization of Dextran-Spermine Conjugates with Cholestic Acid N-hydroxy Succinimide (NHS-Chol, 15)

20.0 mg of Dextran-Spermine conjugate (2, ~26 μmol of free amine, TNBS method) were dissolved in 0.5 ml DDW and diluted with THF (1.0 ml). The mixture was vigorously stirred at room temperature using micro-stirrers and 1–20% mol/mol of stock NHS-Chol solution in anhydrous tetrahydrofuran (THF) was added. The mixture was stirred at room temperature for 24 h and THF was removed by a flush of nitrogen at 40° C. Remaining mixture was freeze-dried and the lyophilizate was suspended in 5.0 ml of diethyl ether to discard unbound Chol groups, filtered and dried in vacuum.

Yield=18.0 mg (~90% w/w).

$^1$H-NMR ($D_2O:d_6$-DMSO 1:1) showed the existing of Cholesterol (Chol) peaks in the region of 0.6–1.2 ppm. Peaks of Dextran-Spermine conjugates were not shifted as a result of hydrophobization.

Content of bound Chol moieties in conjugates was determined by the degree of reduction of amino-functionality using the TNBS method.

$^1$H-NMR technique using external standard (benzene) was used for the determination of Chol moieties in the hydrophobized conjugates.

Hydrophobization of Dextran-Spermine Conjugate with Oleic Acid N-hydroxy Succinimide (NHS-Oleate, 16)

Hydrophobization of Dextran-Spermine conjugate with oleate moieties was prepared in a similar manner to the above, using NHS-Oleate (Sigma®) instead of NHS-Chol.

$^1$H-NMR ($D_2O:d_6$-DMSO 1:1) showed the existing of oleate peaks in the region of 0.87–1.74 ppm.

Content of Oleate moieties in conjugates was determined by the reduction in amino-functionality using the TNBS method.

Synthesis of mPEG2000-PNF 10.0 g of mPEG2000 (5 mmol) were dried over-night with azetropic distillation in toluene (100 ml). The crude was dissolved in anhydrous DCM (25 ml) and TEA (2.8 ml, 4.0 equimolar). The mixture was cooled to 0° C. and 2.8 g of p-nitro-phenyl chloroformate (2.8 equimolar) were added. The mixture was stirred 4 h at 0° C. and 3 days at ROOM TEMPERATURE. Then, 150 ml of DCM were added and the mixture was extracted with DDW (2×50 ml). The organic phase was dried over anhydrous $MgSO_4$, filtered and evaporated to dryness. The resulting oily product was dissolved in small amount of DCM and added dropwise to a large volume of diethyl ether (400 ml) and stored overnight at −20° C. Precipitate were collected by filtration and dried in vacuum over $P_2O_5$.

Yield=9.0 g (~90% by weight to starting PEG).

$^1$H-NMR ($CDCl_3$): 3.566 (m,2H,$CH_3O\underline{CH_2}CH_2$ $(OCH_2CH_2)_nCH_2CH_2OCOPhNO_2$); 3.618–3.793 (m, br, Hydrogen of repeating unit —$(CH_2CH_2O)_n$), 3.892 (m, 2H, $CH_3OCH_2CH_2$ $(OCH_2CH_2)_n\underline{CH_2}CH_2OCOPhNO_2$) and 4.453 (m, 2H, $CH_3OCH_2CH_2(OCH_2CH_2O)_nCH_2$ $\underline{CH_2}OCOPhNO_2$) ppm.

Grafting of mPEG2K-PNF on Dextran-Spermine Conjugates (17)

15.0 mg of Dextran-Spermine conjugate (2, ~19.5 mmol of free amine as determined by the TNBS method) was dissolved in 0.5 ml DDW. To this was added 195 μmol (1% mol/mol) of mPEG2K-PNF (195 μl of a stock in DDW, 1 μmol/μl). The mixture was stirred overnight at ROOM TEMPERATURE. The mixture was purified by G-25 Sepahdex column using water as eluent. Fractions containing product (ninhyrin test detection) were collected and lyophilized to dryness.

Yield=14.0 mg (~90%).

$^1$H-NMR ($D_2O$) failed to identify the existence of grafted PEG chains because the ethyleneglycol units are shifted in the same regions of the polysaccharide hydrogens. A method will be developed for the quantification of grafted PEG chains.

Results and Discussion

Synthesis

Dextran, a naturally occurring poly-β(1–6) dextrose, was oxidized at room temperature with equimolar amount of $KIO_4$. The resulting polyaldehyde was purified by anion-exchange chromatography following extensive dialysis against DDW and lyophilization to dryness. The aldehyde content of oxidized polymers was determined using the hydroxylamine hydrochloride method[17] (table 1).

TABLE 1

Aldehyde content and molecular weight of Dex and oxidized Dex derivatives.

| Polymer code | mole ratio ($KIO_4$: Saccharides) | % di-aldehyde content | Mw | Mn | P |
| --- | --- | --- | --- | --- | --- |
| Dex | — | — | 36,200 | 20,125 | 1.8 |
| Ox:Dex (1:1) | 1:1 | 50 | 24,960 | 14,260 | 1.75 |

TABLE 1-continued

Aldehyde content and molecular weight of Dex and oxidized Dex derivatives.

| Polymer code | mole ratio (KIO$_4$: Saccharides) | % di-aldehyde content | Mw | Mn | P |
|---|---|---|---|---|---|
| Ox:Dex (1:3) | 1:3 | 22 | 28,430 | 15,370 | 1.85 |
| Ox:Dex (1:5) | 1:5 | 14 | 29,960 | 17,830 | 1.68 |

A water solution of oxidized polysaccharide was added dropwise to an equimolar amount of Spermine (naturally occurring tetramine) under basic conditions to obtain the desired imine product (Schiff-base). A sage-metering pump (Model 365) was used to maintain a slow and reproducible rate of addition. The purpose of the slow addition was to minimize crosslinking and to facilitate grafting of Spermine moieties onto the polymer chain. After, sufficient amount of sodium borohydride (5 equimolar excess) was added to obtain the stable amine conjugate. The reduced conjugates were purified by extensive dialysis against DDW, freezed and lyophilized to dryness.

Nearly 250 different polycations were prepared starting from various polysaccharides and oligoamines. Polysaccharides used in this study were the branched Arabinogalactan (20 Kd), linear Pullulan (~50 Kd) and Dextran with 9.3, 18.0, 40, 74 and 500 Kd in molecular weighs. Oligoamines used were mainly Spermine and Spermidine, and more synthetic oligoamines, i.e. polyethyleneimine and various diamines with different lengths. Although, most of these conjugates formed stable complexes with various plasmids as determined by turbidity experiments (data not shown), only certain polycations based on Dextran-Spermine conjugates were found to be active in transfecting cells.

The optimal conditions for the preparation of active Dextran-Spermine conjugates were as the follows:
  1:1 mole ratio between aldehydes and Spermine.
  Initial high basic conditions (pH=11).
  Slow addition of the polyaldehyde to Spermine.
  Sufficient reduction with sodium borohydride.
  Under these conditions, extensive aminolysis of glycoside linkages occurred resulting in drastic chain session and low yields (25–30%).

All polycations were mainly characterized by nitrogen elemental analysis, free amino functionality (TNBS) and molecular weight. Table 2 summarizes a representative group of conjugates (Dextran-Spermine) separately prepared using identical conditions. Nitrogen content of these polycations showed near values in the range of 9.7–12.77. Free amino contents of conjugates were also determined (TNBS method) and found to be in the range of 0.9–1.515 μmol free amine per mg conjugate. Average molecular weights of conjugates were determined by GPC using 3% acetonitril (Acn) in 5% sodium phosphate (pH=4.0) as eluent. The existence of phosphate ions in the mobile phase was found to be important to prevent undesirable interaction between polycations and column resin. All calculated molecular weights were in the region of 6–13 Kd and below the Mw of starting polysaccharide (~36 Kd, table 1). These drastic changes in molecular weight are explained by the extensive aminolysis of glycoside linkages during conjugation step.

TABLE 2 representative Dextran-Spermine conjugates.

| Code | % N [a] | μmol/μg [b] | Mw [c] | Mn [c] | P [c] |
|---|---|---|---|---|---|
| G1-TA-129A | 11.19 | 1.050 | 6,165 | 5,600 | 1.09 |
| G1-TA-6A | 10.37 | 0.930 | 7,080 | 6,600 | 1.07 |
| G1-TA-35/1 | 10.84 | 0.810 | 8,255 | 7,400 | 1.11 |
| G1-TA-40/2 | 7.65 | 0.920 | 6,380 | 5,600 | 1.14 |
| G1-TA-43A | 12.77 | 1.493 | 5,815 | 5,500 | 1.05 |
| Seph17 | 9.91 | 0.960 | 9,940 | 8,000 | 1.24 |
| Seph18 | 10.4 | 1.100 | 9,610 | 8,800 | 1.09 |
| G4-TA-53A | 10.11 | 0.749 | 11,772 | 10,167 | 1.158 |
| G4-TA-53B | 10.04 | 0.785 | 13,328 | 10,858 | 1.228 |
| G4-TA-53C | 10.39 | 0.675 | 14,394 | 11,618 | 1.239 |
| G4-TA-58A | 10.27 | 0.915 | 14,734 | 11,330 | 1.3 |
| G4-TA-58B | 9.71 | 0.766 | 14,535 | 10,398 | 1.398 |
| G4-TA-58C | 9.62 | 0.935 | 13,656 | 11,093 | 1.231 |
| G4-TA-58D | 9.76 | 0.883 | 14,012 | 11,252 | 1.245 |
| G4-TA-58E | 10.03 | 0.982 | 13,631 | 10,570 | 1.289 |
| G4-TA-46IV | 10.76 | 1.115 | ND | ND | ND |
| G4-TA-82 | 12.07 | 1.292 | 11,140 | 9160 | 1.216 |
| G4-TA-96 | ND | 1.576 | 8,856 | 7735 | 1.145 |
| G4-TA-98 | ND | 1.515 | 9,618 | 8543 | 1.126 |
| G4-TA-104 | ND | 1.24 | ND | ND | ND |
| G4-TA-110 | ND | ND | ND | ND | ND |

(i) Found elemental analysis; (b) TNBS method; (c) GPC.

Penetration of complexes (DNA-Polycation) is believed to be the most crucial step in transfection. Hydrophobization of cationic polymers are believed to enhance cell-membrane penetration (indocytosis) and therefore increase in transfection efficacy. In literature, a unique fusogenic group was found to enhance cell penetration of complexes. This group contains two oleate moities (T-shape) connected to the polycation backbone. With the agreement of these findings, we decided to attach our polycations with various fusogenic moities and to investigate their influence on transfection efficacies.

For hydrophobization purposes we used the Chol and Oleate derivatives. NHS active ester derivative of Chol was prepared starting from the commercial Cholesteryl chloroformate and reaction with N-Hydroxy succinimide (NHS) in the presence of DIEA (Scheme 1). Cholesteryl chloroformate is considered to be an extreme reactive derivative and may reacts with primary and secondary amines or even hydroxyl groups yielding a mixture of products. In the contrary, NHS-Chol derivative (Scheme 1) are considered to be a moderate active ester and reacts predominantly with primary amines.

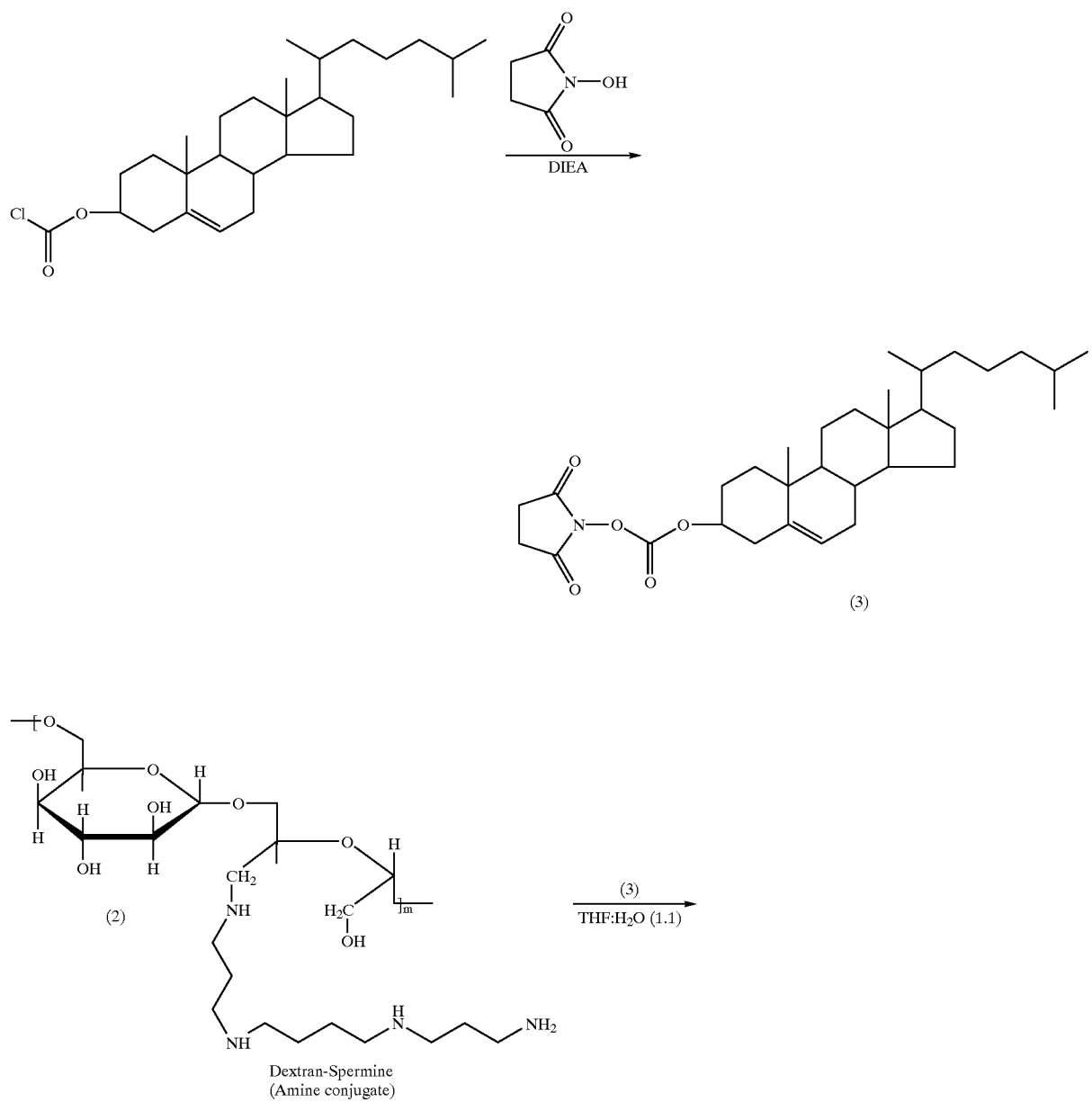
Scheme 1: Synthesis of NHS-Chol (3) and Chol-hydrophobized derivative of Dextran-Spermine conjugate (15).

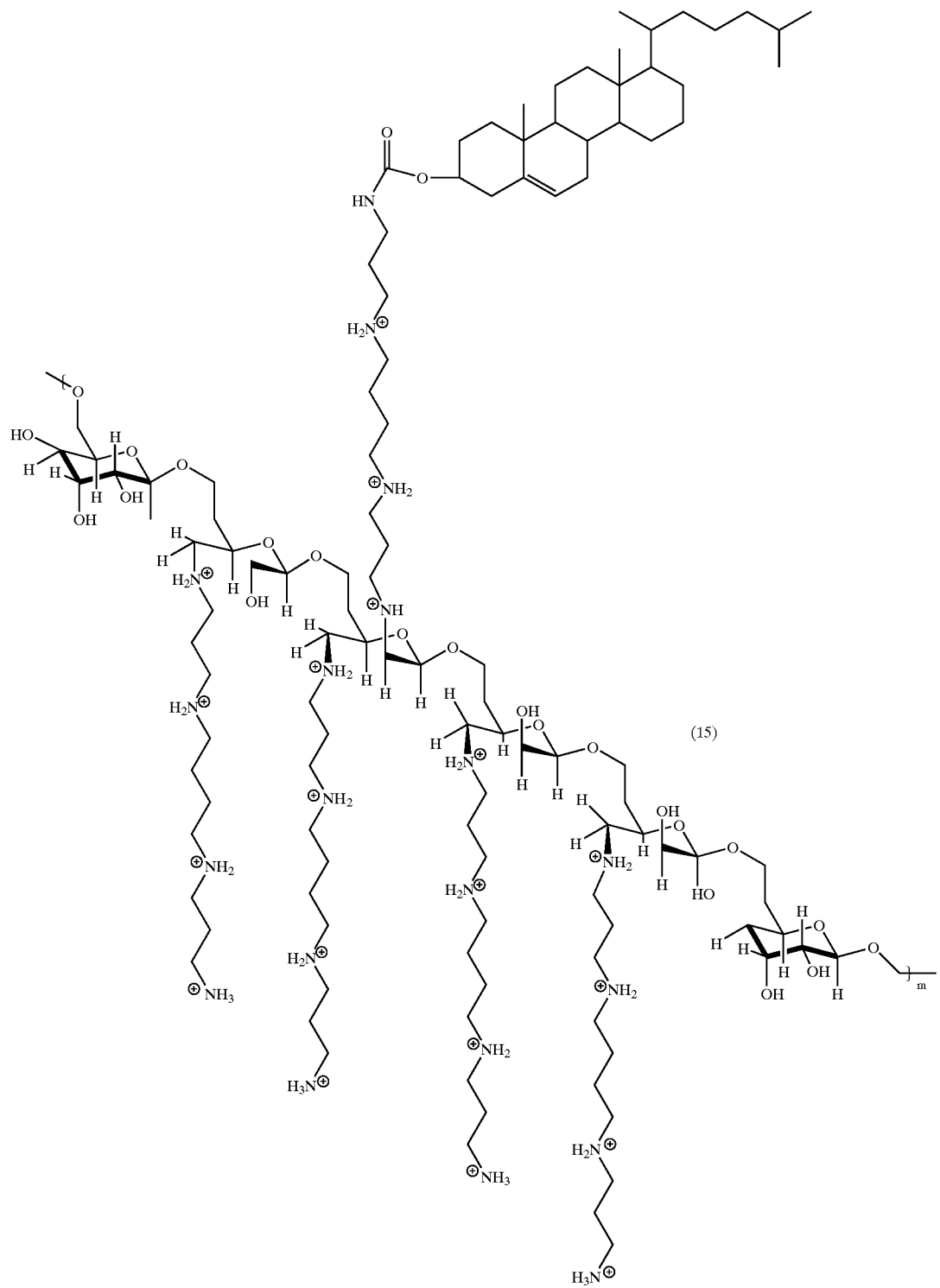
(15)

Hydrophobization of Dextran-Spermine conjugate (Scheme 415) was obtained in a mixture of THF:H$_2$O (2:1) without the use of external base. After, THF was removed and the remaining was lyophilized to dryness. Trituration of the lyophilizate mixture with diethyl ether purified the hydrophobized derivatives of polycations from unreacted Chol moieties. $^1$H-NMR of the Chol-hydrophobized conjugates in a mixture of d$_6$-DMSO:D$_2$O (1:1) showed relative peaks of Chol moieties shifted in the region of 0.6–1.2 ppm. Content of hydrophobization was determined by the reduction in amino content (as a result of amidation) using TNBS method (Table 3). By the same manner, a series of Chol-hydrophobized Dex-Spermine were prepared containing 1–20% mol/mol Cholesterate.

TABLE 3 reduction in free amine content as a function of Chol-hydrophobization.

| Code | % NHS-Chol (mol/mol) | ? mole/mg (TNBS) | % Reduction in free amino content |
|---|---|---|---|
| G4-TA-98 | 0 | 1.515 | 0 |
| G4-TA-100A | 1 | 1.542 | +1.78 |
| G4-TA-100B | 3 | 1.495 | −1.30 |
| G4-TA-100C | 5 | 1.446 | −4.55 |

TABLE 3-continued reduction in free amine content as a function of Chol-hydrophobization.

| Code | % NHS-Chol (mol/mol) | ? mole/mg (TNBS) | % Reduction in free amino content |
|---|---|---|---|
| G4-TA-100D | 10 | 1.308 | −13.66 |
| G4-TA-100E | 20 | 1.178 | −22.25 |

Table 3 summarized the reduction of amino content as a result of Chol-hydrophobization. 1–3% mol/mol hydrophobization (G4-TA-100A and G4-TA-100B) cause no change in TNBS values probably to low and undetected hydrophobization. Higher degree of hydrophobization (5–20% mol/mol, G4-TA-100C to G4-TA-100E) cause to almost a quantatative reduction in amino content indicating a complete amidation.

Hydrophobization of Dextran-Spermine conjugate with oleate derivative (Scheme 5, 16) was obtained in a similar way to 15. The starting polycation (2) was mixed in THF:H$_2$O (2:1) solution, with a commercial or synthetic NHS-Oleate. Unreacted oleate moieties were purified as in 15 by triturating the lyophilizate in diethyl ether.

Oleate content of hydrophobized polycation's was also determined by the reduction of amino content using TNBS method (table 4).

Unlike the starting polycations, which gives a clear solution in water, hydrophobized polycations (Oleate and chloesterate) produced a turbid solution probably due to reduction in solubility caused by hydrophobization.

Scheme 2: Synthesis of Oleate-hydrophobized derivative of Dextran-Spermine conjugate (16).

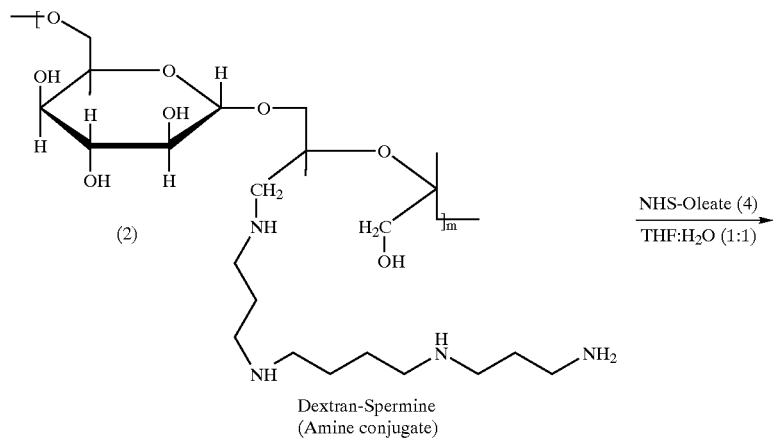

Dextran-Spermine
(Amine conjugate)

-continued
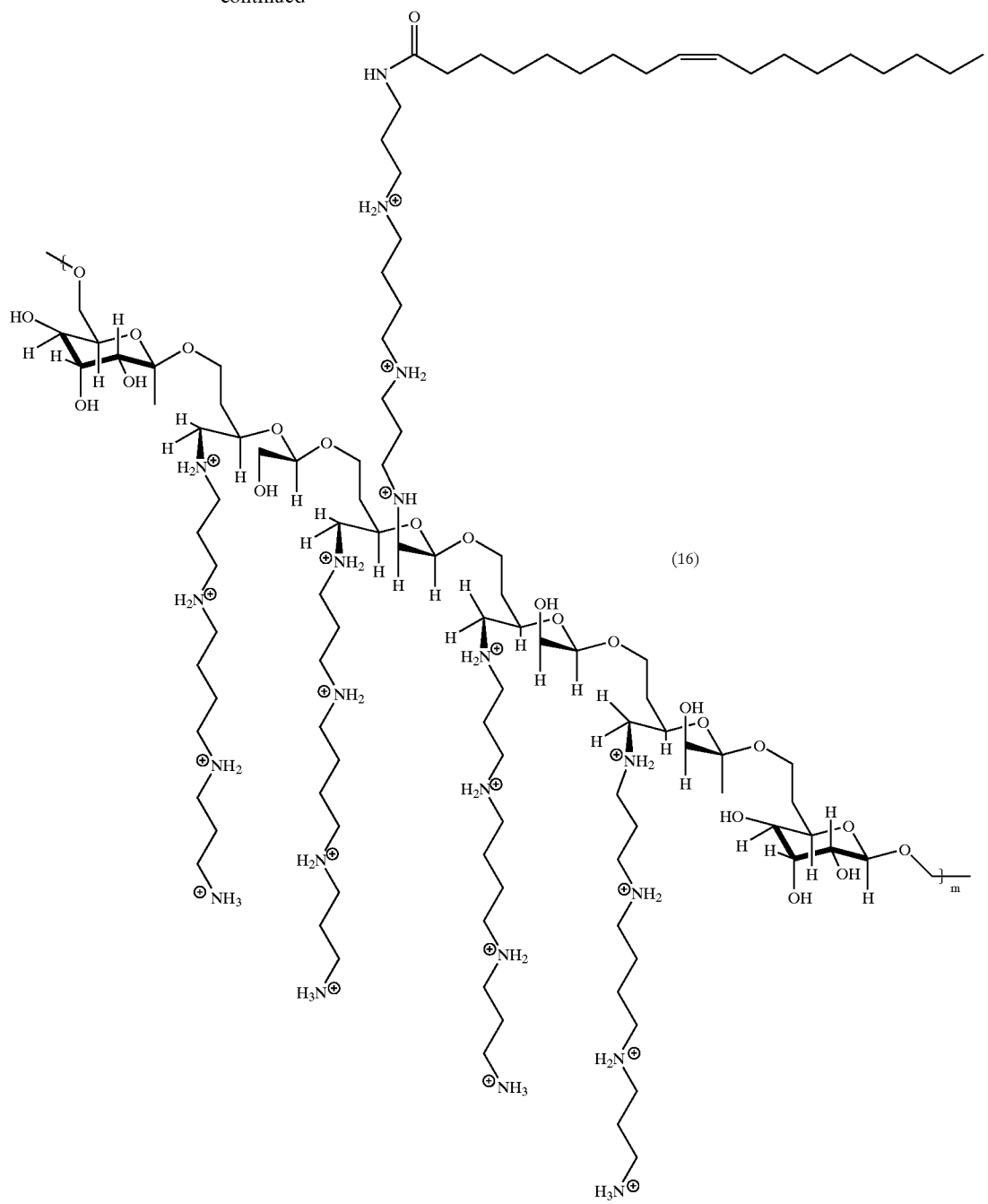
(16)
As in Chol-hydrophobization, table 4 summarizes the reduction of amino content as a result of Oleate-
TABLE 4
reduction in free amine content as a function of Oleate-hydrophobization.
| Code | % NHS-Oleate (mol/mol) | ? mole/mg (TNBS) | % Reduction in free amino content |
|---|---|---|---|
| G4-TA-98 | 0 | 1.515 | 0 |
| G4-TA-105C | 5 | 1.463 | −3.44 |
| G4-TA-105D | 10 | 1.339 | −11.62 |
| G4-TA-105E | 20 | 1.224 | −19.20 | hydrophobization. Hydrophobized polycations (5–20% mol/mol, G4-TA-105C to G4-TA-105E) cause to almost a quantitative reduction in amino content indicating a complete amidation.

described earlier and attached to the desired polycation in a mixture of THF:DDW medium. Scheme 3 illustrates a possible structure of Dextran-Spermine polycation hydrophobized with saturated fatty acids.

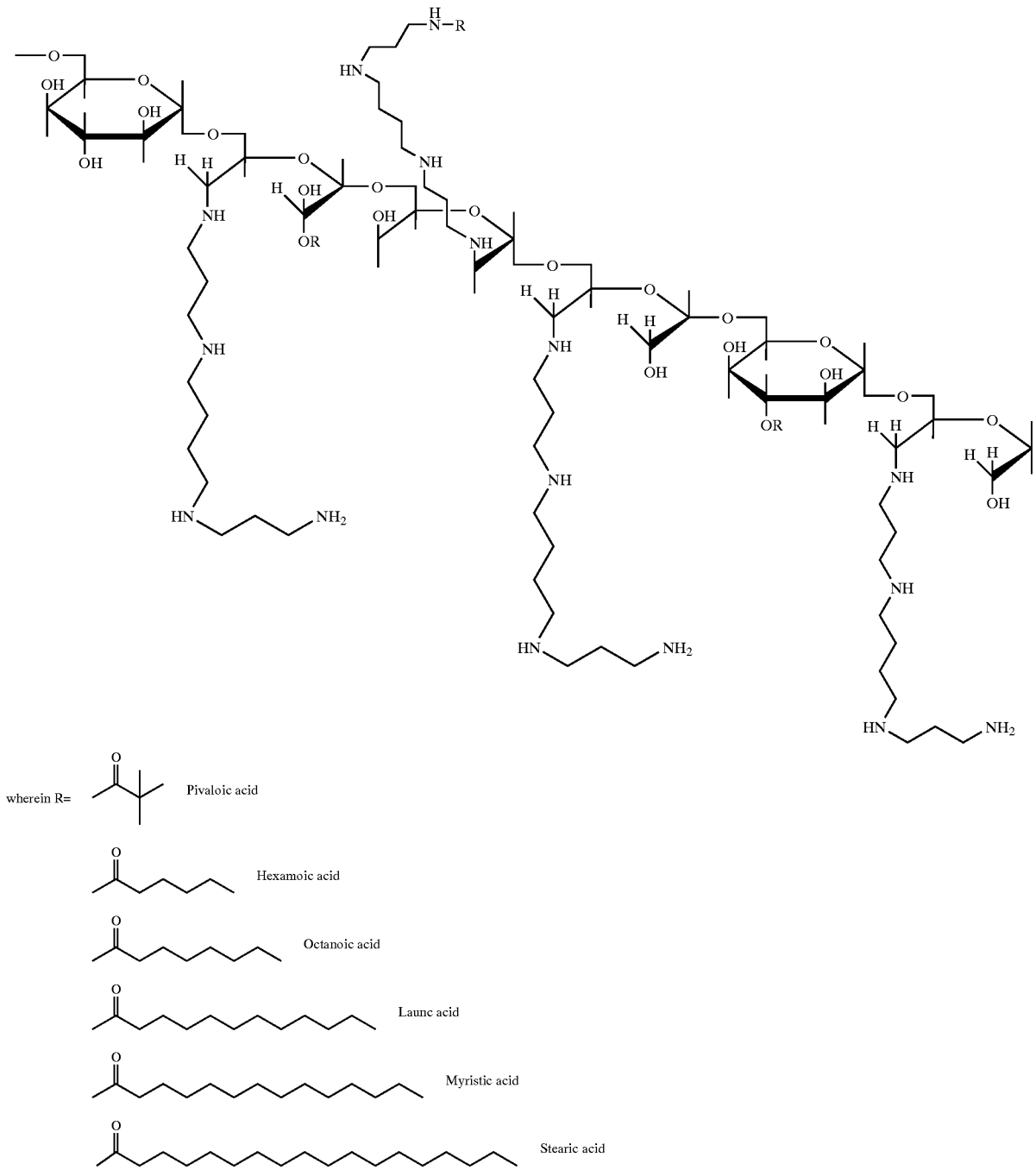

Dextran-Spermine was also hydrophobized by other fatty acid. These acids include: Pivaloic (C5-branched), Hexanoic (C6-linear), Octanoic (C8-linear), Lauric (C12-linear), Myristic (C14-linear) and Stearic acid (C18-linear). These acids were converted to their NHS active ester derivatives as Unsatured fatty acids (oleic, linoleic and linolenic) were also derivatized to their NHS active ester and attached in a similar way to Dextran-Spermine conjugates (Scheme 4).

Also, T-shape active esters containing hydrophobic moieties (Cholesterate or oleate) in each side were developed and used for hydrophobization (Scheme 5

Scheme 4: Unsaturated fatty acid grafted onto polycation
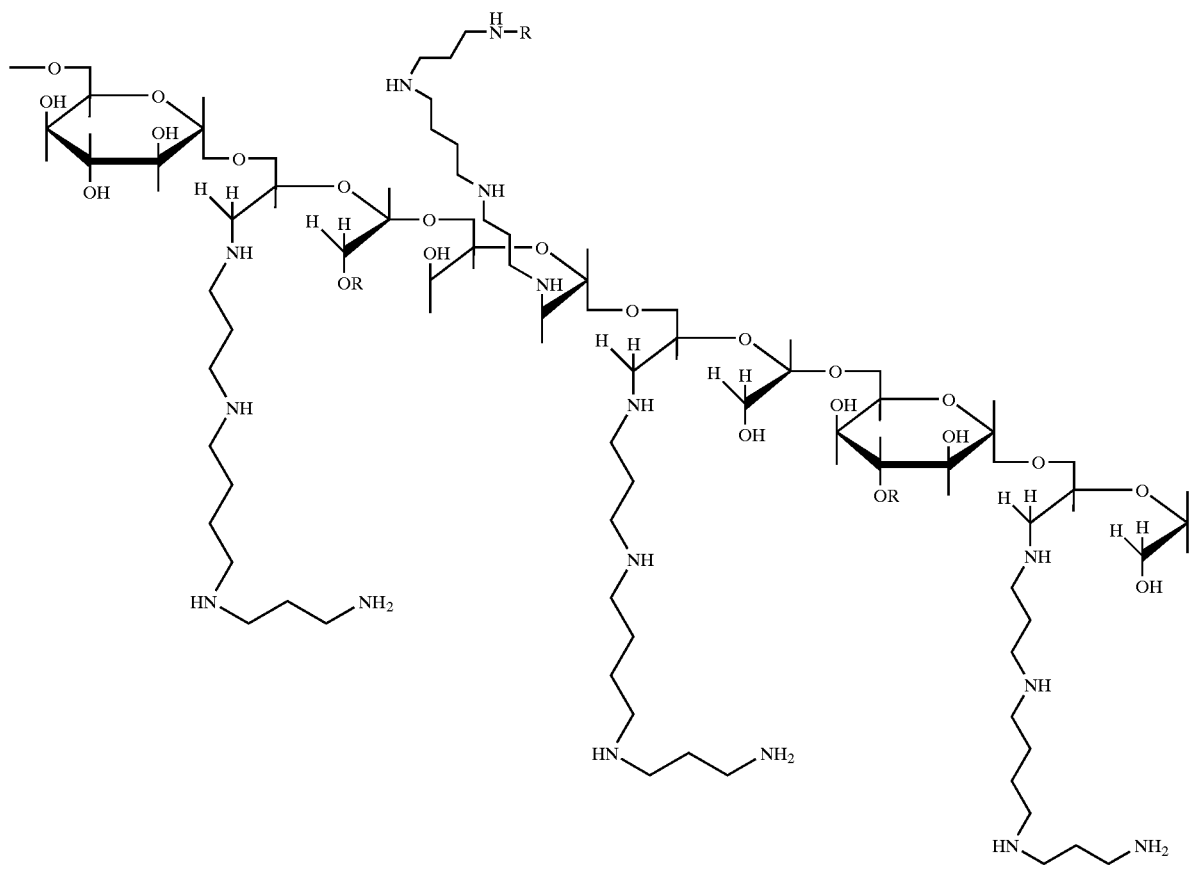
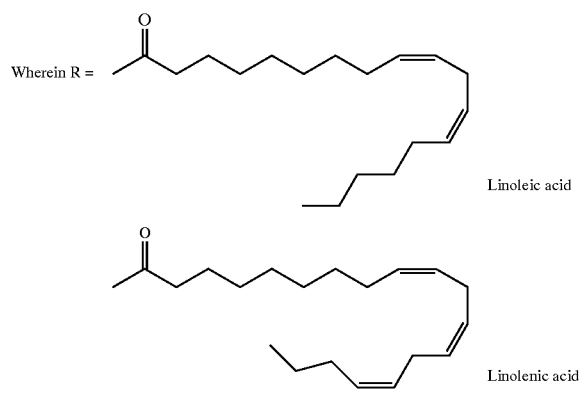
Wherein R =
Linoleic acid
Linolenic acid and 6). In brief, L-Lysine-O-methyl ester dihydrochloride was reacted with 2.2 equimoles of Cholesteryl chloroformate or Oleic acid N-hydroxy succinimide, in the presence of TEA as hydrochloride acceptor. The resulted diChol-L-Lysine-O-methyl ester or diOleate-L-Lysine-O-methyl ester, were converted to their active esters according to the procedure described in experimental section.

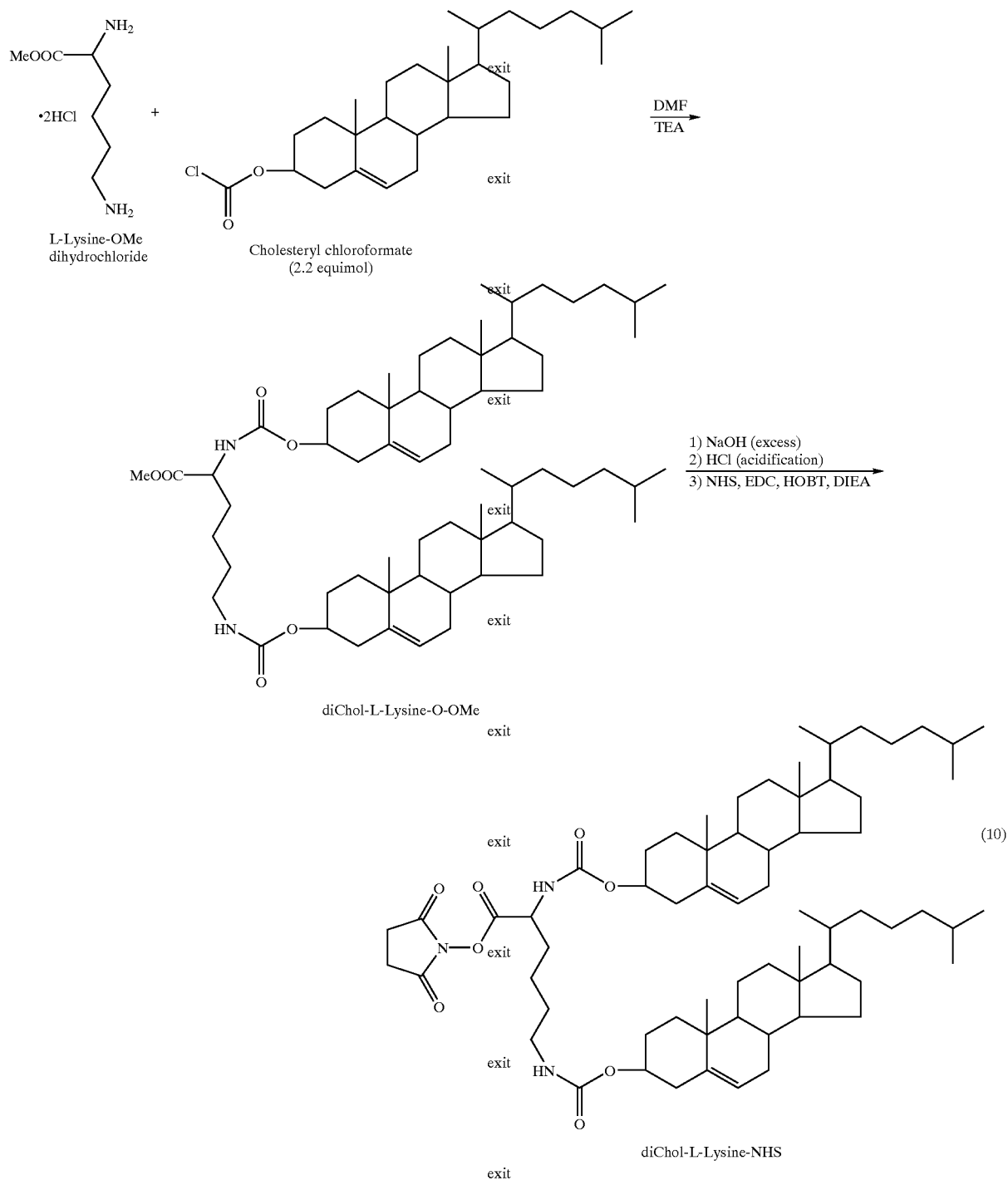

Scheme 5: Synthesis of diChol-L-Lysine-NHS (10).

diOleate-L-Lysine-O-methyl ester, were converted to their active esters according to the procedure described in experimental section.
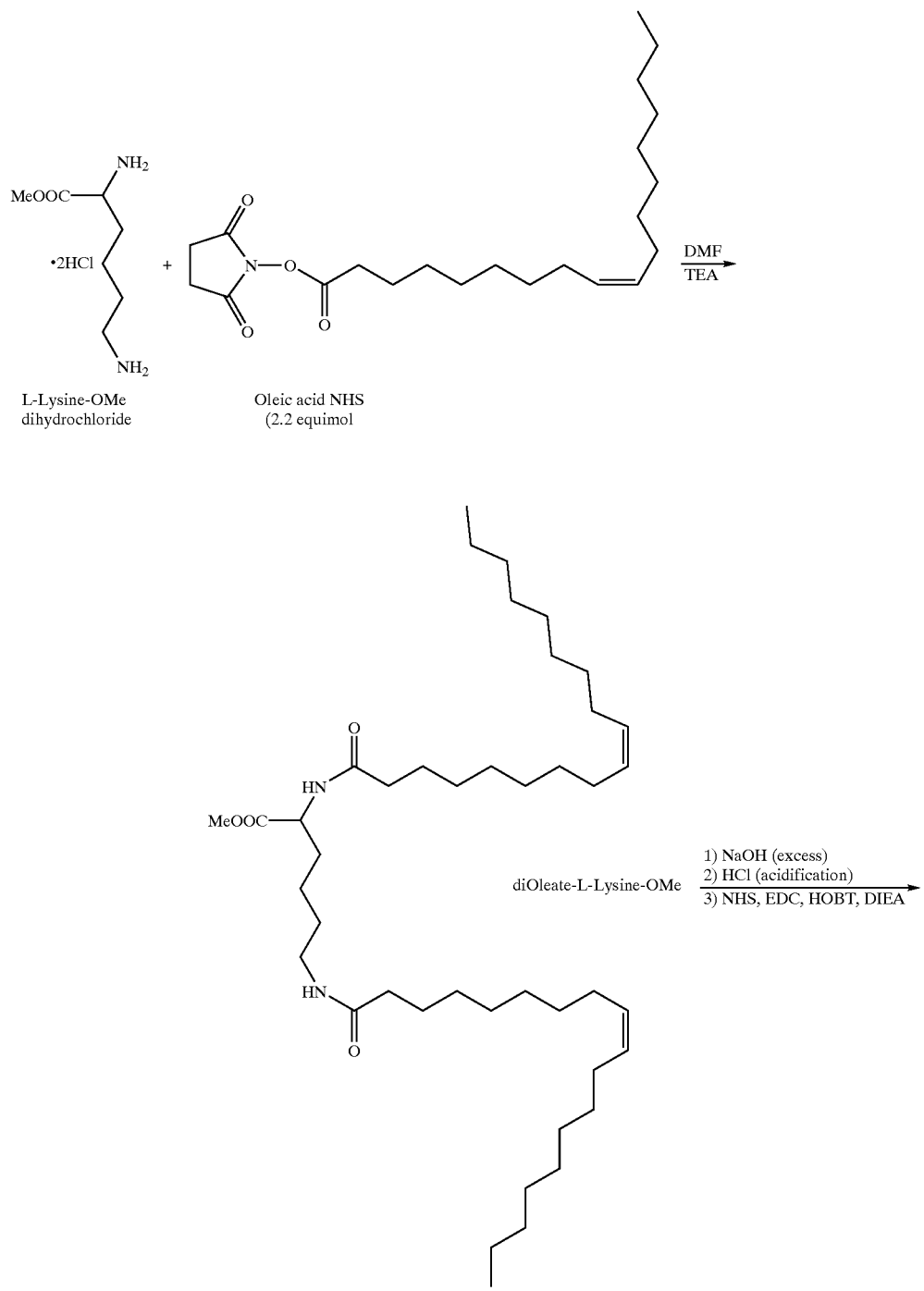

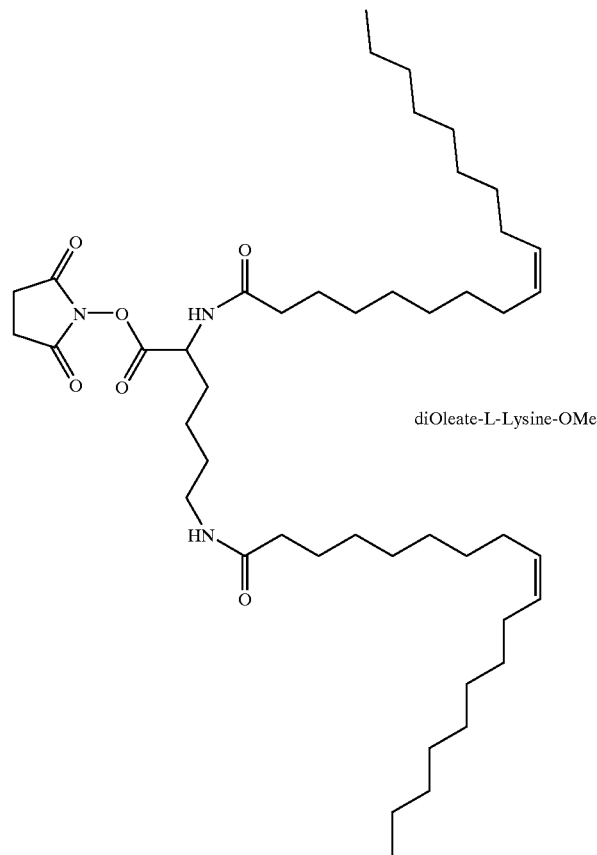
diOleate-L-Lysine-OMe
Sxheme 6: Synthesis of diOleate-L-Lysine-NHS.
Hydrophobization of Dextran-Spermine conjugate (2) with the diChol-L-Lysine-NHS or diOleate-L-Lysine-NHS (Scheme 9) will be prepared as described in 8 and 9. Unreacted diChol moieties will be also discarded from the hydrophobized conjugates by triturating the lyophilizate product with diethyl ether.

Scheme 7: Hydrophobization of
Dextran-Spermine with diOLeate-L-Lysine NHS.

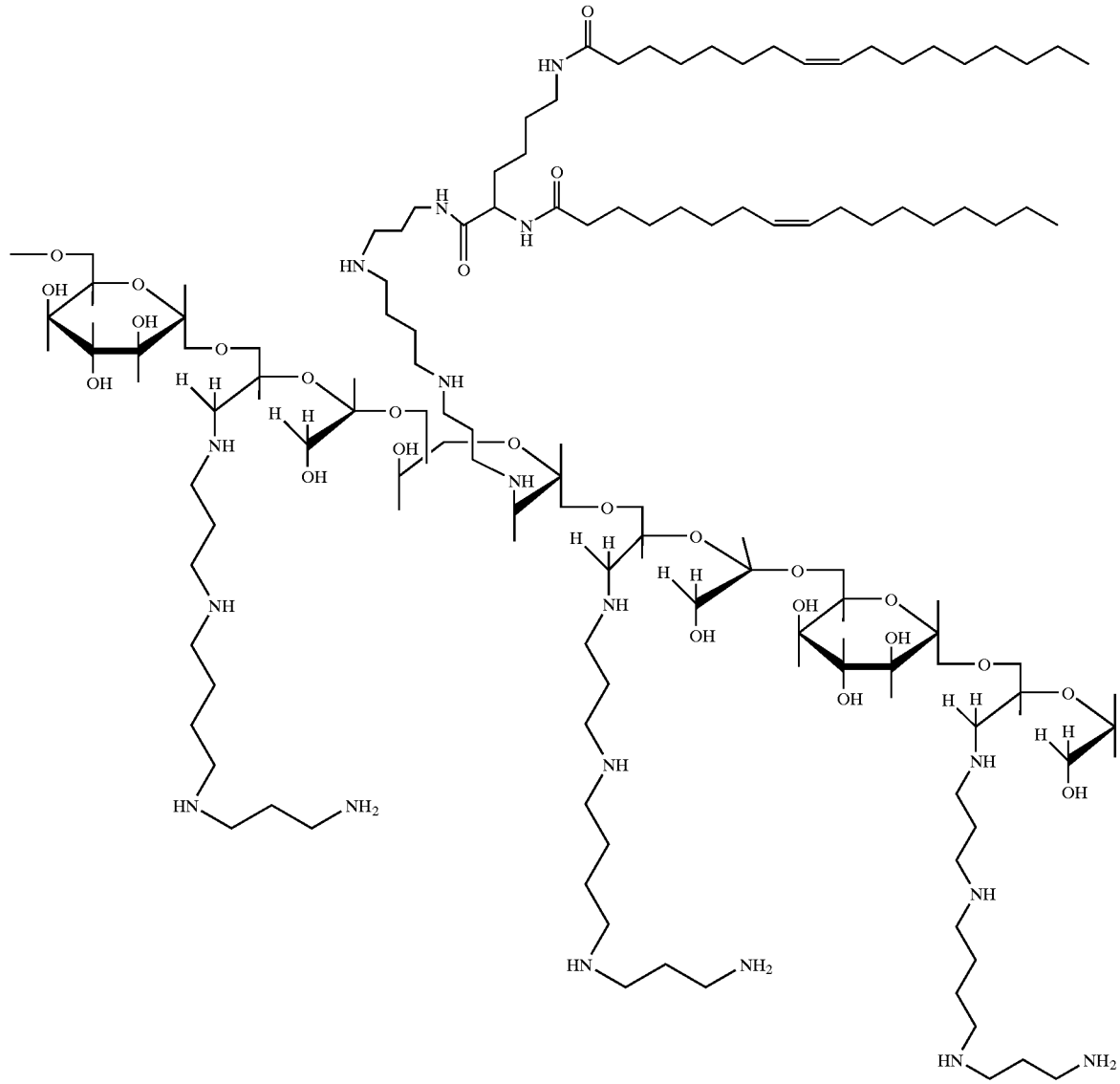

The complexes of DNA formed with simple cationic polymers, similarly to other colloidal particles (e.g., lipososmes) show very low stability in bloodstream[21-22]. They are rapidly removed from bloodstream by RES, which decreases their potential for specific targeting in-vivo. It has been proposed that an interaction of the complexes with plasma proteins can be the major obstacle in their successful in-vivo use. In analogy with stealth liposomes[23-24].

Polyethylene glycols (PEGs) are considered to be attractive for this purpose. They are safe, non-toxic, cheap and do not interact with plasma components. For purpose of attachment of PEG chain onto the polycation, we prepared an active ester of PEG capable for direct conjugation to free amino functionality. In brief, monomethyl ether PEG2000 (mPEG2000) was reacted under anhydrous conditions with p-nitro-phenyl-chloroformate in the presence of TEA as base. The resulting mPEG2000-PNF was isolated in pure form by precipitation in large volume of diethyl ether. The degree of modification was found to be 100% as shown in $^1$H-NMR. The active ester was then reacted with the polycation (2) in DDW and at room temperature. The resulting grafted-PEG polycation (Scheme 10) was purified by sephadex G-25 column chromatography using DDW as eluent.

The overall yield was nearly 85%.

Scheme 8: Grafted-PEG Dextran-Spermine conjugate.

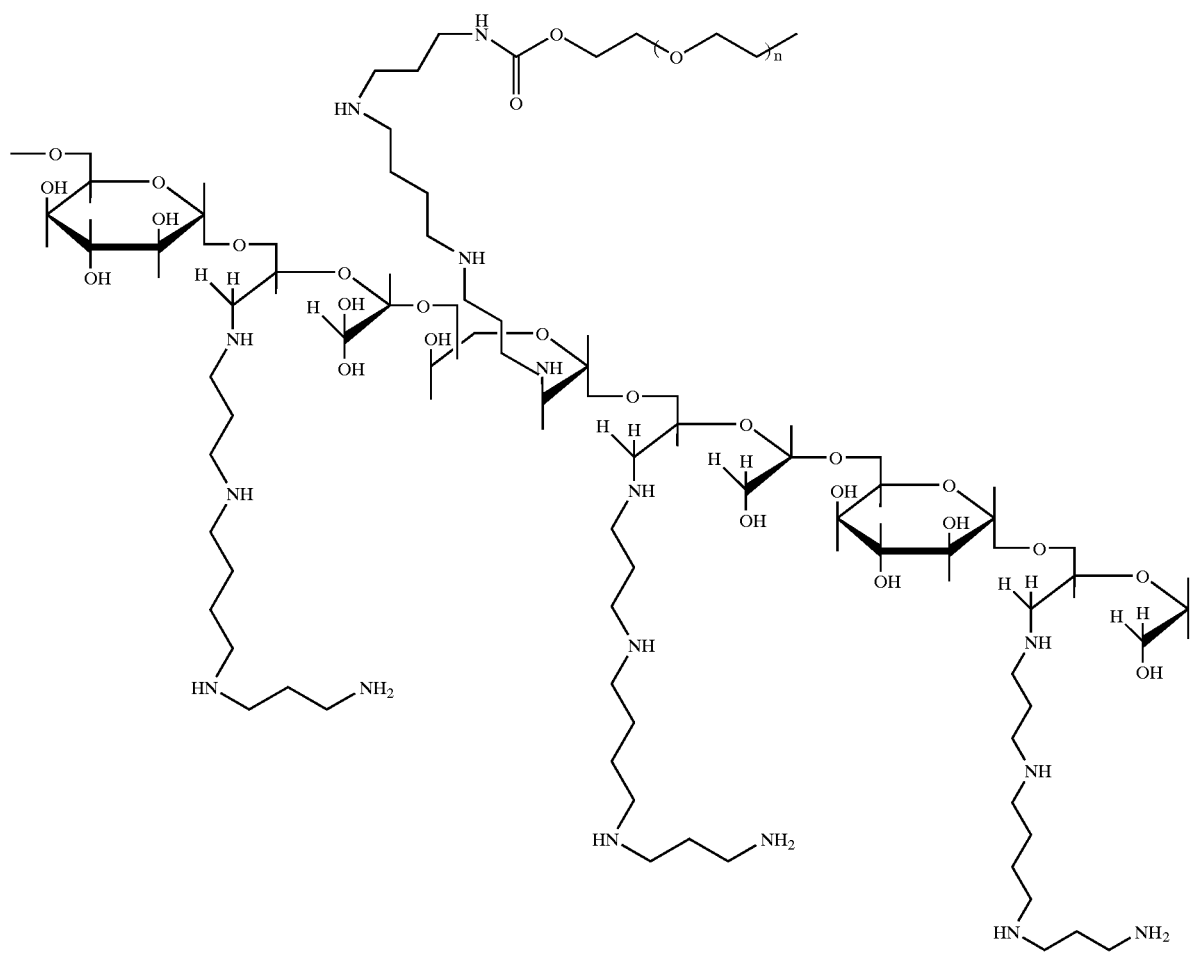

EXAMPLE 2

Hydrazide Derivatives

Preparation of Hydrazide-oligoamine Derivatives for Conjugation to Polysaccharides Hydrazine derivatives (R—NHNH$_2$) are attractive compounds for the purpose of reductive-amination. The resulting hydrazone bond (R—NHN=CR') is considered to be much stable than simple imine (R—N=CR'). Hydrazide-oligoamine derivatives were synthesized and attached to oxidized dextran.

a) Spermine-hydrazide

TriBoc-Spermine were mixed with ethyl bromoacetate and the resulting product was treated with hydrazine hydrochloride to obtain the hydrazide product:

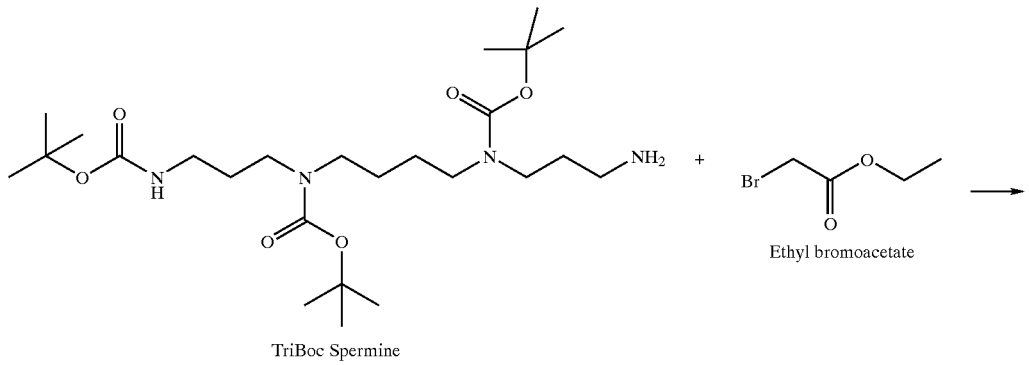

TriBoc Spermine

Ethyl bromoacetate

-continued

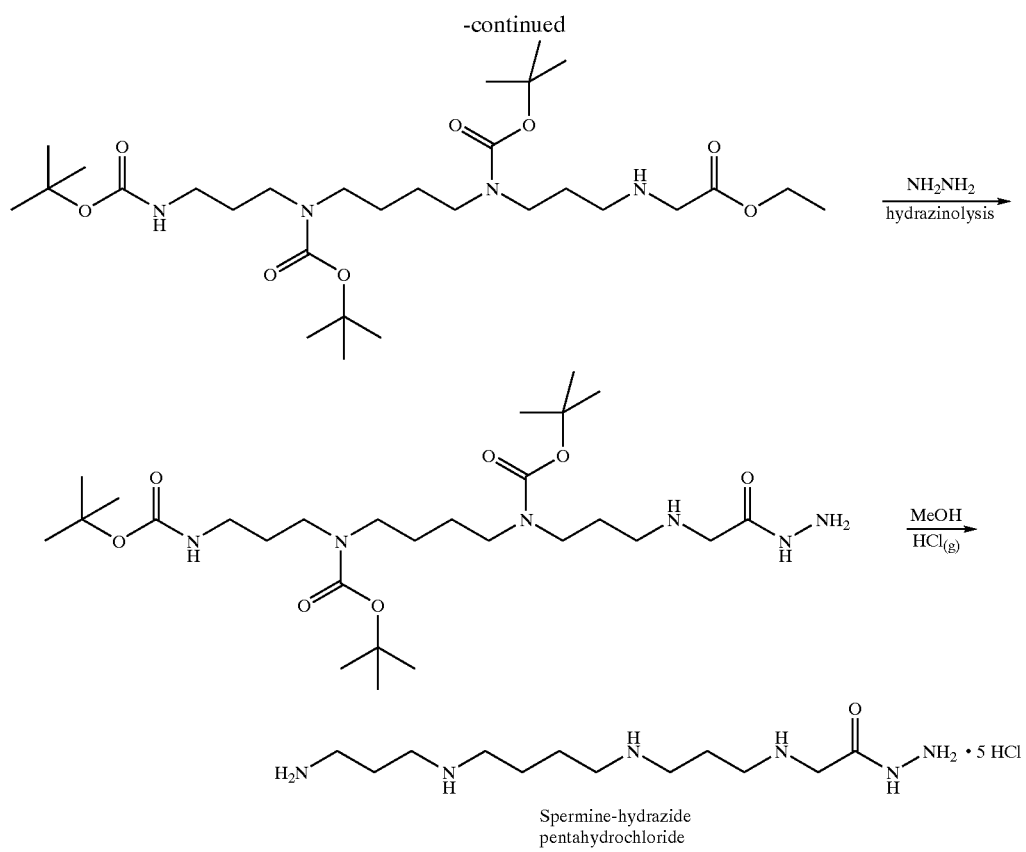

Spermine-hydrazide pentahydrochloride b) Lysine-hydrazide

L-Lysine-OMe was Bocylated using di-tert butyl dicarobonate to the corresponding di-Boc-L-Lysine-OMe. The obtained product was treated with excess of hydrazine and the protecting group (Boc) is removed using gaseous HCl.

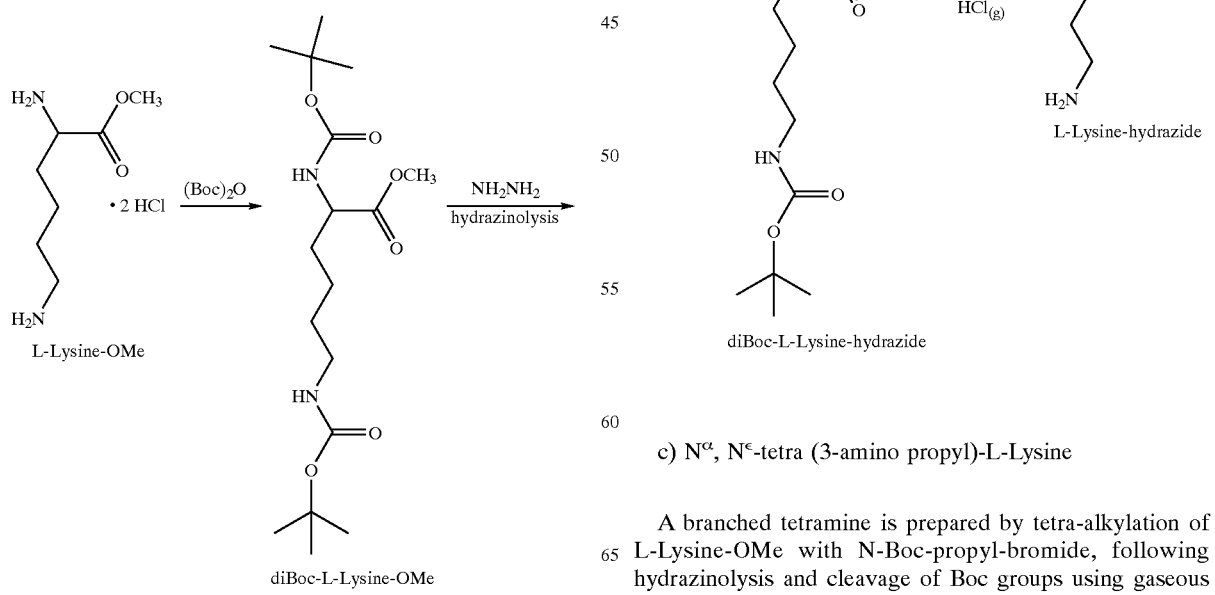

c) $N^\alpha$, $N^\epsilon$-tetra (3-amino propyl)-L-Lysine

A branched tetramine is prepared by tetra-alkylation of L-Lysine-OMe with N-Boc-propyl-bromide, following hydrazinolysis and cleavage of Boc groups using gaseous HCl in dry methanol.

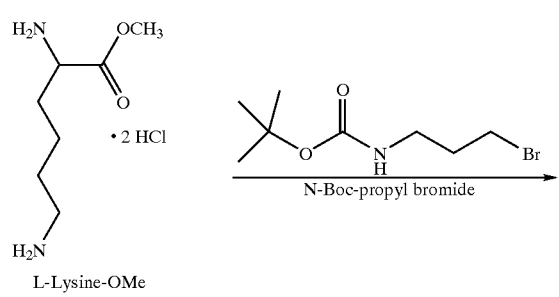

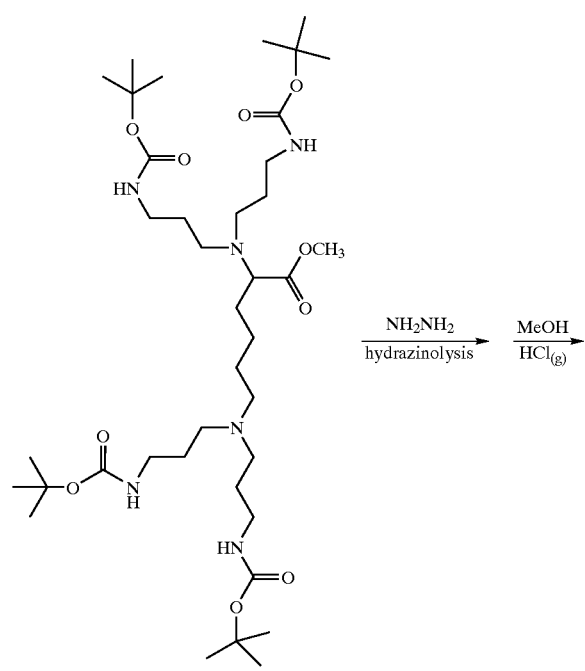

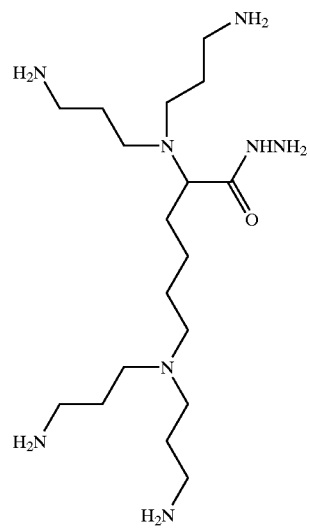

Nα,Nε-tetra (3-amino propyl)-L-Lysine-hydrazide d) (L-arginine)-hydrazide drivative

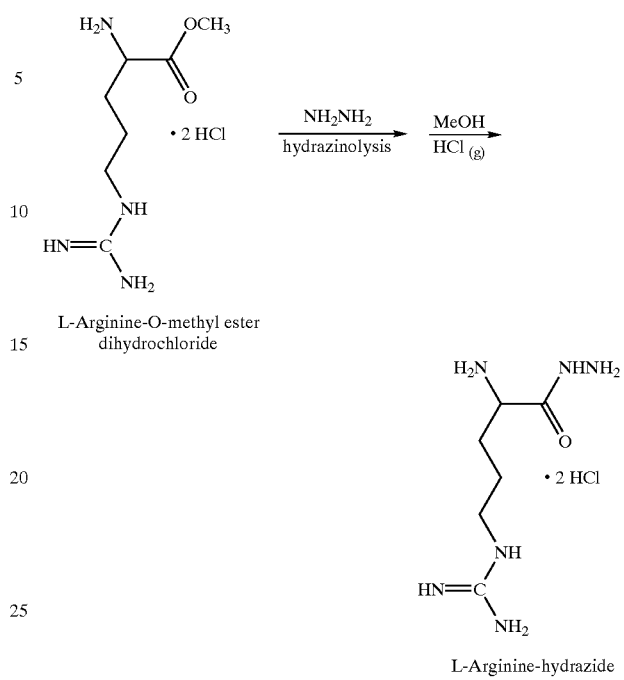

EXAMPLE 3

Combination of Quaternary and Regular Spermine in Conjugates

Totally quaternarized polycations gave no transfection activity probably due to strong complexation and large aggregate size of formed complex (>10,000 nm). Thus mixtures of 10%, 20% or 30% of quaternarized spermine was used in combination to native spermine in conjugation to dextran and other polysaccharides. Under these conditions, quaternary spermine functions as the major complexing units and regular spermine functions as a buffering system.

EXAMPLE 4

Synthesis of Hydrophilic Headgroup of Quaternary Spermine

Monoquaternary spermine containing hydrophilic headgroup was prepared in a similar way to compound 3. Briefly, TriBoc-Spermine was reacted with excess of 1-azido-3-iodo-propane in the presence of excess TBA. The resulting quaternarized derivative was hydrogenised under (Pd—C) and Boc protecting group were removed using gaseous HCl in dry methanol.

The hydrophilic-mono-quaternary Spermine was attached to polyaldehydes under the classical method (reductive amination described above).

EXAMPLE 5

Targeting Experiments

Ligand for targeting purposes were conjugated to active polycations with tetraethylene glycol as spacer-arm. These ligands include: mannose, glusose and galactose for targeting to liver cells, or folic acid and avidin for targeting to certain cancer cells.

EXAMPLE 6

Conjugation to the Polysaccharide Chain

Oxidized dextran (45% degree of oxidation) was reacted with oleylamine, at a ratio of 1, 5, and 10 oleylamine per 50 saccharide units, in water: tetrahydrofuran 1:1 v/v mixture at room temperature. After 5 hours of stirring, spermine was added to the mixture at a 1:1 molar ratio to the remaining aldehyde groups along with excess of cyanoborohydride as reducing agents. The reaction was continued at room temperature over night-and the polycation was purified by dialysis or Sephadex chromatography to yield hydrophobized polycation at an overall yield of 75%. A similar procedure was used for the preparation of polycations made from butanediamine, spermidine, and oligoethylene imine, Mw=600.

Other methods for conjugation of fatty groups onto a polysaccharide include the reaction of oleoyl chloride with the hydroxyl groups of either oxidized or non-oxidized dextran or arabinogalactan in a water:THF mixture at room temperature. In a typical experiment, dextran (100 mg) is dispersed in water:THF 1:1 v/v mixture containing 10 mg of sodium bicarbonate (10 ml) and a THF solution of oleoyl chloride (10 mg in 1 ml THF) was added and mixed rapidly for two hours. After 2 hours 10 ml THF was added and the reaction continued for another 3 hours. The mixture was lyophilized to dryness and the white residue was purified by precipitation in methanol from water. The hydrophobized oxidized dextrean was then reacted with spermine or spermidine by reductive amination at a aldehyde:amine 1:1 ratio to obtain the desired cationic polymer.

Hydrophobic or hydrophilic residues can be conjugated to polysacharide units by tosylate or mesylate activation of the hydroxyl groups on the polysaccharides.

EXAMPLE 7

Chitosan-oligoamine Derivatives

Spermine and spermidine were conjugated to chitosan by reacting N-ethyliodide spermine with chitosan in a mixture of water pH5 and THF at a 1:1 v/v ratio. Fatty chains were conjugated to the polymer in a similar way by reacting oleyl chloride with chitosan or spermine chitosan under similar conditions.

EXAMPLE 8

Grafting of Hydrophobic or Amphiphilic Residues

The attachment of hydrophobic or amphiphilic residues can be carried-out by various methods adopted from the literature (for example, Y. Takakura, et al. Control of pharmaceutical properties of soybean tyrosine inhibitor by conjugation with dextran I: synthesis and characterization, J. Pharm. Sci. 78, 117–121, 1989; G. H. Hermanson, Bioconjugate techniques, Academic Press, 1996). The following methods were used by the present inventor.

The hydrophobic residue was generally conjugated by an ester, amide, imine, amine, urethane or carbonate bonds depending on the availability of the functional groups on the conjugated component. For example, fatty acids such as hexanoic acid or oleic acid are bound to hydroxyl or amine groups on the polymer carrier using activated acids such as anhydride or acid chloride derivatives or activating agents such as dicyclohexylcarbodiimide (DCC) and its derivatives that are more suitable for aqueous mediums. Alternatively, hexyl or oleyl alcohols or amines have been conjugated via carbonate or urethane bonds using phosgene derivatives. Polyethylene glycol oligomers and derivatives were conjugated either directly via the hydroxyl end or by converting the hydroxyl end group to a carboxylic acid (by reacting the alcohol with succinic, glutaric or maleic anhydride) or to a reactive epoxide group (by reacting with epichlorhydrine). The grafting reactions are conducted in hydrophilic solutions where the polymer carrier is soluble in or at least dispersed in fine particles with large surface area. Typical mediums are dimethylformamide (DMF), N-methyl pyrrolidone, dimethylsulfoxide (DMSO) and their mixtures with water.

The amount of grafting suitable for cell penetration and transfection is in the range of 1 to 10% of the repeated units building the polymer carrier, i.e. saccharide units. This amount is dependent on the nature of the attached group, the nature of the final product and the polymer carrier.

In a typical experiment Triton-X100 (7 g, 10 mmol) was dried by azeotropic distillation with toluene. After solvent evaporation, $SnCl4$ (5 ?I) and epichlorhydrin (1.4 g, 15 mmol) and the mixture was kept at 100° C. overnight. The solvent was evaporated and mixed with ether and extracted with cold 1N NaOH. The etheric layer was dried over $MgSO4$ and evaporated to dryness to yield the epoxy terminated Triton (70% yield). The product was identified by TLC (silica, toluene:chloroform) and by H NMR (aromatic protons 5.9–6.7 ppm).

Alternatively, dry Triton-X100 was reacted with succinic anhydride (1:1.1 mole ratio) in toluene at reflux overnight to yield the corresponding succinate derivative as determined by H-NMR, IR and titration.

The chloroformate derivative of Triton was prepared from the reaction of the hydroxyl terminal with diphosgene using known procedures. Grafting of these functionalized Triton was conducted in DMF or DMF:water solutions under the proper conditions. For example, epoxide terminated Triton (0.5 g) was reacted with dextran (2 g) in 1 N NaOH (10 ml) overnight at room temperature. The polymer was purified by dialysis against water and lyophilization. The derivatization rate was about 5% of the saccharide groups.

Carboxylic acid Triton-X100 reacted with arabinogalactan in a mixture of DMF and water using water soluble DCC. Chloroformate Triton was reacted with a suspension of polysaccharides in dry DMF for 3 days at room temperature. Triton was reacted in access relative to the saccharide groups in order to obtain a 5% conjugation.

Similar procedures were applied for the conjugation of methoxy-PEG-OH or Lipo-PEG (a diblock polymer of a fatty acid such as stearyl, oleyl or hexanoyl groups with $(PEG)_{10-100}$).

The conjugation of highly hydrophobic residues such as fatty acids and cholesterol to hydrophilic polysaccharides was conducted in an organic solvent such as DMF or DMSO, the conjugation yield was low (1–5% of saccharide units) but suitable for gene formulation.

Hydrophobic or amphiphilic residues were conjugated to oxidized polysaccharide via an amine or imine bonds. In this cases, the hydroxyl terminal of Triton and PEG derivatives were converted to amino terminals by esterification with glycine or alanine or by replacing the hydroxyl group with an amine using the tosylate/ammonia procedure as described below for the amination of polysaccharides.

The amine terminated PEG derivatives, cholesteryl amine or fatty amines are reacted with oxidized polysaccharides in basic buffer solutions (pH9–11) or mixtures of DMF with water over night, similar to the procedures used for the grafting of spermine. The grafting can be conducted during the conjugation of the oligoamines by adding both the oligoamine and the amphiphilic derivative to the reaction mixture. The imine derivatives were hydrogenated to the corresponding amine bond using NaBH4 in water for 24 hours at room temperature.

EXAMPLE 9

Oleic Acid Modification of Low Activity Spermine-dextran Polymers

The purpose of this experiment was to show that hydrophobization improves significantly the transfection yield.

Ten batches of spermine-dextran conjugates of molecular weights between 15,000 and 25,000, nitrogen content between 7–11% w/w and various branching degrees (20 to 60% branching) were conjugated with oleic acid at a 20% of the free amino side chains of the conjugated spermine. The conjugation procedure was as described above. Five of these polymers showed a high transfection activity while the other 5 showed a medium or low transfection efficiencies.

In this study, dextran-spermidine (3 amino groups) was derivatized with 20% oleic acid using the above procedure, Another experiment was conducted to determine the effect of crosslinking on the trasnfection efficacy. The reaction between oxidized dextran and spermine was conducted at concentrated solutions which increases crosslinking. Insoluble crosslinked polymer particles of 1 to about 100 microns which were used for transfection studies.

Transfection studies using the methods described below show a significant increase in the transfection efficiency for all polymers which was higher or comparable to the efficacy obtained with DOTAP/Cholesterol lipid system. The crosslinking decreased the efficacy compared to the branched polymers usually obtained.

EXAMPLE 10

Transfection Experiments

General Procedure 1 ml of cell suspension at the concentration of 6*10$^5$ cells/ml was preincubated for 24 h in 6 wells dish, after adherence the medium was replaced by 1 ml SFM (Serum Free Medium). Either polyplexes or lipoplexes were added to the dish for 4 h, then SFM was replaced by 1 ml complete medium and the cells undergo incubation for 20 more hours. Two different kinds of plasmid DNA were used (pCMV-β encoding to production of β-gal enzyme and pCMVhGH encoding to the production of human growth hormone). We also used 2 different kind of cells (NIH and EPC).

In Vitro Transfection Using pCMV-β and EPC Cells.

We used 6*10$^5$ EPC cells per well in L-15 medium. The amount of pCMV-β plasmid in complex was 2 μg per well and the amount of polymer (G4TA46/IV, G4TA82) was vary between 5.5–24 μg. We used dotap/cholesterol as control. All incubation were done at 20° C. Quantification of β-gal enzyme produced by the cells was done by β-gal elisa kit.

In Vitro Transfection Using pCMV-hGH and NIH Cells.

1.3*10$^5$ NIH cells per well in DMEM medium was used. The amount of pCMV-hGH plasmid in complex was 1.62 μg per well and the amount of polymer (TA1-129A, G1TA6A) was vary between 5.5–22 μg. Dotap/cholesterol was used as control. All incubations were at 37° C. Quantification of hGH produced by the cells was done by hGH elisa kit.

a. Transfection efficacies of different polycations prepared from various polysaccharides and oligoamines.

Cells: HEK293.

Plasmid: GFP.

Tested Polycations: PEI600, AG-PEI, D-PEI, D-Spermidine, AG-Sperminem, D-Spermine, P-Spermine.

Control: Calcium Phosphate

Results:

Most of tested polycations possesed low to modarate transfection efficiency. Only one polycation (TA1-129A) was found to be very active. This polycation is composed of Dextran-Spermine conjugate of about 10,000 molecular weight and nitrogen content of about 10%. The transfection efficacy of TA1-129A was compared to the tested control (calcium phosphate) and found to be in the same range. The % transfection was determined visually by fluorescence microscopy, counting fluorescenting cells in a certain field.

b. Transfection efficacy of TA1-129A in comparison to the commercial Transfast® and Calcium phosphate.

Cells: HEK293, HeLa human cancer cells

Plasmid: GFP.

Tested Polycations: TA1-129A composed of unique Dextran-Spermine conjugate.

Control: Transfast® and Calcium phosphate.

Results:

Transfection efficacy of TA1-129A was not affected by the presence/absence of glycerol. Transfection efficacy of TA1-129A was found to be in the same range as in Transfast® and Calcium phosphate. The % of cells transfected using plasmid:TA1-129A at a 0.2, 0.1, 0.07 and 0.05 nucleotide:nitrogen molar ration was 15, 38, 17, and 34% for the experiment with glycerol shock and 18, 47, 20, and 42% without glycerol shock, respectively. Transfast and calcium phosphate showed 40 and 46% transfection yield, respectively. HeLa cells were used in this study for the purpose to demonstrate that the efficacy of transfection c. Transfection efficacy of TA1-129A and G1-TA6 in NIH-3T3 cells.

Cells: NIH-3T3.

Plasmid: hGH-CMV (Human Growth Hormone).

Tested Polycations: Dextran-Spermine conjugates similarly prepared in two different batches (TA1-129A and G1-TA6).

Control: commercial cationic liposome (DOTAP-Chol 1:1, Avanti®).

Content of liberated h-GH protein was quantified using a commercial h-GH Elisa kit.

Results:

Transfection efficacy of TA1-129A and G1-TA6 was found to be in the same range as in DOTAP:Chol (1:1).

Maximum transfection was found in 0.1–0.05 (−/+), charge ratio. Around 22 to 28 ng/ml of hGH were quantified in this range of charge ratio.

The relative transfection of several batches of the optimal polymer in several ratios (−/+) in comparison with the values obtained for dotap/chol in each experiment. Data for TA1-129A and G1TA6A obtained from transfection in NIH cells using pCMVhGH, and dotap/chol as control. Data for G4TA82 obtained from transfection in EPC cells using pCMVβ, and dotap/chol as control. The relative transfection activity was 150%, 170%, and 280% for TA1-129A, G1TA6A, and G4TA82, respectively (Dotap/cholesterol is 100%).

A high transfection yield of more than 40% was obtained when using HeLa cells d. Effect of Oleate moieties on transfection.
Cells: HEK293.
Plasmid: GFP.
Tested Polycations: Dextran-Spermine (G4-TA-82, G4-TA-96, G4-TA-98, G4-TA-104 and G4-TA-110) and oleate-hydrophobiozed Dextran-Spermine (10% and 20% mol/mol).
Results:
All non-hydrophobized polycations (G4-TA-82, G4-TA-96, G4-TA-98, G4-TA-104 and G4-TA-110) gave the best transfection values at 0.1 charge ratio (–/+). Hydrophobized polycations (10% or 20% oleate, mol/mol) gave the best transfection efficacy at 0.25 charge ratio (–/+).
Hydrophobized polycations remarkably increase transfection, by at least 2 fold.

e. Effect of Oleate moieties on transfection (batch #1).
Cells: HEK293.
Plasmid: x-Gal.
Tested Polycations: Dextran-Spermine (G4-TA-98) and hydrophobiozed G4-TA-98 containing 1–20% mol/mol oleate (batch #1).
Content of liberated x-Gal protein was quantified using a commercial x-Gal Elisa kit in 10% serum containing medium.
Results:
0 and 1% oleate (mol/mol) gave no transfection. This is explained by the high serum content which cause a remarkable decomplexation and hence in drastic decrease in transfection efficacy.
3 and 5% (mol/mol) oleate gave low transfection values probably due to partial-extent stabilization of oleate moieties.
Higher oleate content (10 and 20%, mol/mol) gave the best transfection values. These excellent transfection values were found to be similar to the values obtained from Fugen®.

f. Effect of Oleate moieties on transfection (batch #2).
Cells: HEK293.
Plasmid: x-Gal.
Tested Polycations: Dextran-Spermine (G4-TA-98) and hydrophobiozed G4-TA-98 containing 1–20% mol/mol oleate (batch #2).
Content of liberated x-Gal protein was quantified using a commercial x-Gal Elisa kit in 10% serum containing medium.
Results:
Similar data were obtained as in batch #1.
Increasing the oleate content from 5 to 20% gave a remarkable increase in tranfection values. A transfection yield (determined by the optical density of the formed b-Gal dye) of the 0, 10, 20, and 30 % oleate per primary amino groups was 0.35, 0.62, 1.42, and 0.2, respectively.
At 30% (mol/mol) a decrease in transfection value was obtained. This could be explained by the high oleate content which results in slow decomplexation and hence decrease in transfection.

g. Effect of Other Fatty Moieties on Transfection.
Cells: HEK293.
Plasmid: GFP.
Tested Polycations: Dextran-Spermine (G4-TA-82) and stearate, myristate, and octanoate-hydrophobiozed Dextran-Spermine (10% and 20% mol/mol).
Results:
All hydrophobized spermine-dextran polycations gave transfection values at 0.2 charge ratio (–/+). Hydrophobized polycations (10% or 20% fatty chain, mol/mol) gave the best transfection efficacy at 0.25 charge ratio (–/+). Hydrophobized polycations remarkably increase transfection, by at least 2 fold. However, the fatty acid side groups, stearate, octanoate, and myristate were less active than oleate derivatives.

h. Transfection Efficacies of Hydrophobized Dextran-Spermine as a Function of Serum Content in Medium.
Cells: NIH-3T3.
Plasmid: x-Gal.
Tested Polycations: Dextran-Spermine (G4-TA-98) and hydrophobized G4-TA-98 containing 1–20% mol/mol oleate (batch #2). The
Content of liberated x-Gal protein was quantified (Pg/ml) using a commercial x-Gal Elisa kit in 10% serum containing medium. Results: The results are given in the following Table.

TABLE 5

Effect of serum on the transfection efficacy of oleate bearing spermine-Dex.

| Polymer | x-Gal protein (Pg/ml) | | |
|---|---|---|---|
| % oleic acid (+/– ratio) | 0% serum | 25% serum | 50% serum |
| 0%, 0.1 | 370 | 10 | 10 |
| 10%, 0.25 | 120 | 800 | 130 |
| 20%, 0.25 | 180 | 1600 | 250 |
| Dotap/chol 1:1, 0.5 | 150 | 200 | 10 |

As can be seen, the oleate had a dramatic effect on the transfection yield in serum. These results indicate that fatty acid chain may improve the in-vivo transfection yield.

EXAMPLE 11

Toxicity In-vitro.

Procedure

200 µl of cell suspension at the concentration of $2.5*10^4$ cells/ml was preincubated for 24 h in 96 wells dish. Different concentration of polyplexes (complexes of G4TA46/IV or G4TA82 with DNA) and different amount of polymer were added to the wells. Complexes of dotap/chol were used as control. The charge ratio (–/+) that was chosen for this experiment was the one that gave the best results in transfection in vitro (G4TA82 0.2 (–/+), G4TA46/IV (–/+)). 36 h post transfection the cells undergo fixation with glutaraldehyde and stained with methylene blue. U.V measurement at 620 nm indicate the vitality of the cells (high value of O.D indicate low toxicity). The polymers did not affect the cell viability at concentrations of 1–6 microgram per ml. To the contrary, Dotap/cholesterol killed about 50% of the cells at concentrations of less than 1 micgram/ml with more than 80% at concentrations of 3 microgram per ml.

EXAMPLE 12

Toxicity In-vitro 11

Procedure

200 µl of cell suspension at the concentration of $2*10^4$ cells/ml was preincubated for 24 h in 96 wells dish. Different concentration of polyplexes (complexes of G4TA98 or G4TA98-10%-ol, G4TA98–20%-ol with DNA) and different amount of polymer were added to the wells. We used complexes of dotap/chol as control. The charge ratio (−/+) that was chosen for this experiment was the one that gave the best results in transfection in vitro (G4TA82 0.2 (−/+), G4TA98 0.1 (−/+), G4TA98, 10, 20% OL 0.25 (−/+). DOTAP/CHOL 0.5 (−/+)). 42 h post transfection the cells undergo fixation with glutaraldehyde and stained with methylene blue. U.V measurement at 620 nm indicate the vitality of the cells (high value of O.D indicate low toxicity). Similar results were obtained which indicates that the polymers are safe to cells at the transfection concentrations.

EXAMPLE 13

Transfection In Vivo

Transplantation of Matrices Containing Complexes in Mice

Matrices of chitosan crosslinked with 20% arabinogalactan and absorbed them with complexes that were prepared from the optimal polymer-DNA, dotap/chol-DNA or naked DNA. pCMVP at the amount of 70 µg were loaded into each matrix. The matrices were transplanted subcutaneous in C3H/HEN mice. 4 weeks post transplantation the area around the matrix was stained. The X-gal staining results showed qualitative expression of β-gal enzyme in all groups.

Injection of Complexes to Fish

Archocentrus nigrofaciatum fish at approximate weight of 5 g were used. Complexes contain G5TA46/IV-DNA at 2 different ratios (1.28 (−/+), 0.64 (−/+)), lipoplexes contain dotap/chol-DNA and naked DNA were injected to the dorsal muscle (2 µg pCMVβ per fish). 5 days post injection the fish were sacrificed and were tested for presence of β-gal enzyme by staining. Again the X-gal staining results showed qualitative expression of β-gal enzyme in all groups.

EXAMPLE 14

Other Applications for Polysaccharide-oligoamine Conjugates of this Invention:

The polycations described in this application were used for a range of applications as follows:

i. Complexation with heparin

Aqueous solutions of Heparin and arabinogalactan-spermine were mixed at a 1:1 cation to anion ratio for a few hours at room temperature. The formed complex was lyophilized to form a white powder which when dispersed in water very little free heparin was found in the solution. This system can be used for control concentration of heparins in aqueous solutions both in vitro and in vivo.

ii. Combination with hyaluronic acid

Aqueous solutions of hyaluronic acid (MW=2 million daltons, 1% solution) and arabinogalactan-spermine (MW=20,000, 5%) were mixed at a 10:1 and 1:1 anion to cation ratio for a few hours at room temperature. A significant increase in the viscosity of hyaluronic acid was obtained which was used for the injection of condors cells in mice for cell growth and cartilage formation. The 1:1 mixture became more viscous than the 10% mixture. Alternatively, the formed complex was lyophilized to form a white porous matrix which when dispersed in a medium containing condors cells, the matrix particles swelled and allowed the cell ingrowth into the swollen matrix.

Other anionic polymers such as alginic acid, carboxymethyl cellulose and a 1:1 copolymer of acrylic acid and methyl methacrylate (Eugragit) formed an electrostatic complex with the spermine-dextran or arabinogalactan conjugates.

iii. Scaffolds for cell growth were prepared by conjugating a concentrated solutions of spermine and oxidized arabinogalactan at a amine:aldehyde ratio of 1:20, 1:10 and 1:5 at room temperature. After 24 hours of mixing the resulting compound was freeze dried to form a white porous matrix suitable for cell growth for tissue engineering purposes.

iv. Non-medical applications for these polycations was found in the design of electronic circuits based on repeated alternating coating of monolayers of cationic polymers and anionic polymers. The polycations of this invention are used in other applications in electro-optics and conducting polymers where cationic polymers are used.

A different application is the use of the cationic polymer as semi-natural conditioner which is composed of a polycation polymer. The high water solubility, the safety and easy to make makes this class of polycations ideal for cosmetic and toiletry applications.

These polycations can replace polycations that are used in the printing industry, paper industry and others.

EXAMPLE 15

Conjugation of Dansylhydrazine Onto Dextran-Spermine

Dansylhydrazine (available from Aldrich Chemicals) was mixed with spermine at a ratio between 1 and 10 mole % and reacted with oxidized dextran (50% degree of oxidation) in water solution as described above. A high yield of Dansyl conjugation to the polymer was obtained. This dansyl derivative can improve the interaction with cell membranes which improves transfection of genes or cell attachment.

Another procedure was used for the conjugation of dansyl chloride onto the spermine-dextran conjugate where the dansyl chloride was mixed with a solution of spermine-dextran in tetrahydrofural-water 1:1 mixture.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

EXAMPLE 16

Biodegradation of the Polycations

In-vitro Degradation of Spermine-dextran

Experimental: spermine-dextran polymers were weighted and incubated in phosphate buffer 0.1M, pH=7.4 at 37° C. At fixed time points the molecular weight of the polymers was determined by GPC and by viscosity measurements. The extent of degradation was determined as the percentage of the molecular weight loss over time.

Results: There is a slow degradation of the polymers in aqueous solution in-vitro. After 4 weeks in buffer solution the polymers decreased in molecular weight by about 40% with the 20% oleate derivatives degraded the least.

In-vivo Implantation and Histological Observation of Chitosan-AG Gels in BALB/c Mice:

Experimental: Scaffolds of crosslinked spermine-dextran and Oxycell® (as a reference compound) were implanted sub-cutaneously in the back of BALB/c mice. The scaffolds at size of 5×5 mm were sterilized by U.V., and soaked in sterile saline solution prior to implantation. After 3 days, 1 and 4 weeks the mice were sacrificed and the scaffolds were explanted without loss from the mice together with the surrounding tissue. Following fixation with 10% formalin the gels were sectioned and stained with haematoxylin-eosin.

Results: The scaffolds cause local reaction at the surrounding tissue as can be seen after 3 days and one week, however this reaction disappear after one month and can no longer be seen at the surrounding tissue. After one month a significant amount of the polymer was-degraded and eliminated from the implantation site.

What is claimed is:

1. A polycation compound comprising:
   a) a natural or synthetic polysaccharide chain having an amount of saccharide ranging from 2 to 2000 saccharide units;
   b) at least one oligoamine grafted covalently to the polysaccharide chain per each segment of 5 saccharide units, wherein the oligoamine is a linear, branched or cyclic alkyl amine having at least two amino groups; and
   c) at least one further grafted group which is either a hydrophobic group or an amphiphilic group grafted covalently to the polysaccharide chain per each segment of 50 saccharide units, wherein the hydrophobic group or amphiphilic group includes an aliphatic chain of at least 4 carbon atoms.

2. A biodegradable polycation complex with a polyanion comprising:
   a) a natural or synthetic polysaccharide chain having an amount of saccharide ranging from 2 to 2000 saccharide units;
   b) at least one oligoamine grafted covalently to the polysaccharide chain per each segment of 5 saccharide units, wherein the oligoamine is a linear, branched or cyclic alkyl amine having at least two amino groups; and
   c) at least one further grafted group which is either a hydrophobic group or an amphiphilic group grafted covalently to the polysaccharide chain per each segment of 50 saccharide units, wherein the hydrophobic or amphiphilic group includes an aliphatic chain of at least 4 carbon atoms; and
   wherein the hydrophobic or amphiphilic group is complexed with an anionic macromolecule selected from the group consisting of polynucleic acids, proteins and polysaccharides that are anionic.

3. A biodegradable polycation according to claim 2, wherein the anionic macromolecule is selected from the group consisting of a plasmid, an open chain polynucleic acid, an oligonucleotide, an antisense, a peptide, a protein, a polysaccharide and combinations thereof.

4. A biodegradable polycation compound according to claim 1, wherein the polysaccharide chain is selected from the group consisting of dextrans, arabinogalactan, pullulan, cellulose, cellobios, inulin, chitosan, alginates and hyaluronic acid, wherein the polysaccharide chain contains an amount of saccharide ranging from 2 to 2000 saccharide units.

5. A biodegradable polycation compound according to claim 1, wherein the saccharide units in a synthetic polysaccharide are connected by a bond selected from the group consisting of acetal, hemiacetal, ketal, orthoester, amide, ester, carbonate and carbamate bonds.

6. A biodegradable polycation compound according to claim 1, wherein the polysaccharide is a synthetic polysaccharide formed from the condensation of an aldaric acid and a diaminoalkane.

7. A biodegradable polycation compound according to claim 1, wherein the grafted oligoamine is grafted to the polysaccharide chain by a bond selected from the group consisting of an amine bond, an imine bond, an amide bond and a carbamate bond.

8. A biodegradable polycation compound according to claim 1, wherein the oligoamine has the formula:

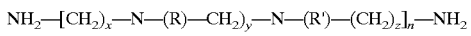

wherein x, y, z are integers between 0 and 4 and x+y+z is between 1 and 4 and n is at least 1 when x+y+z=2 or more, or at least 2 when x+y+z=1 and wherein R and R' groups are H or an aliphatic group of 1 to 6 carbons.

9. A biodegradable polycation compound according to claim 1, wherein the oligoamine is a peptide of up to 20 amino acids with at least 50% of the amino acids are cationic including lysine, ornithine, and arginine.

10. A biodegradable polycation compound according to claim 1, wherein the oligoamine is selected from the group consisting of spermine and alkyl-substituted spermine, wherein the alkyl substituent contains 1–6 carbons.

11. A biodegradable polycation compound according to claim 1, wherein the oligoamine is a linear or branched ethyleneimine oligomer having up to 10 ethylene imine units.

12. A biodegradable polycation compound according to claim 1, having an amphiphilic residue wherein the amphiphilic residue is selected from the group consisting of fatty chains, phospholipids, cholesterols, ethylene glycol oligomers, propylene glycol oligomers and combinations thereof.

13. A biodegradable polycation compound according to claim 12, wherein the ethylene and propylene glycol oligomers have a fatty chain block on one side.

14. A biodegradable polycation compound according to claim 12, wherein the amphiphilic residue is connected to the polysaccharide chain by a bond selected from the group consisting of an amine, amide, imine, ester, ether, urea, carbamate and carbonate bonds.

15. A biodegradable polycation compound according to claim 12, wherein the amphiphilic residue is an oleic chain.

16. A biodegradable polycation compound according to claim 12, wherein the amphiphilic residue facilitates the crossing of the polycation through biological membranes.

17. A biodegradable polycation compound according to claim 1, wherein the polycation composition is not toxic or immunogenic.

18. A biodegradable polycation compound according to claim 1, wherein the composition further comprises a ligand for facilitating the binding of the composition to a cell or tissue.

19. A biodegradable compound according to claim 1, in combination with cationic and nonionic lipids or polymers for enhanced cell transfection.

20. A biodegradable compound according to claim 1, wherein the polycation has a structure selected from the group consisting of a comb-like chain, a branched chain and a cross-linked chain.

21. A pharmaceutical composition, comprising the complex of claim 2, in combination with a pharmaceutically acceptable carrier.

22. A pharmaceutical composition of claim 21, in combination with a biodegradable polymer matrix or capsule for controlled, timed and extended delivery of the complex.

23. A porous matrix suitable as a scaffold for cell growth comprising a porous scaffold suitable for attachment of cells, wherein the scaffold is formed of a polycation composition comprising
   a) a polysaccharide chain having an amount of saccharide ranging from 2 to 2000 saccharide units;
   b) at least one oligoamine grafted covalently to the polysaccharide chain per each segment of 5 saccharide units, wherein the oligoamine is a linear, branched or cyclic alkyl amine having at least two amino groups; and
   c) at least one further grafted group which is either a hydrophobic group or an amphiphilic group grafted covalently to the polysaccharide chain per each segment of 50 saccharide units, wherein the hydrophobic group or amphiphilic group includes an aliphatic chain of at least 4 carbon atoms.

24. The compound of claim 1 in the form of a coating comprising:
   a) a polysaccharide chain having an amount of saccharide ranging from 2 to 2000 saccharide units;
   b) at least one oligoamine grafted covalently to the polysaccharide chain per each segment of the saccharide units, wherein the oligoamine is a linear, branched or cyclic alkyl amine having at least two amino groups; and
   c) at least one further grafted group which is either a hydrophobic group or an amphiphilic group grafted covalently to the polysaccharide chain per each segment of 50 saccharide units, wherein the hydrophobic group or amphiphilic group includes an aliphatic chain of at least 4 carbon atoms.

25. A biodegradable complex according to claim 2, in combination with cationic and nonionic lipids or polymers for enhanced cell transfection.

26. A biodegradable complex according to claim 2, wherein the polycation has a structure selected from the group consisting of a comb-like chain, a branched chain and a cross-linked chain.

* * * * *

UNITED STATES PATENT AND TRADEMARK OFFICE
CERTIFICATE OF CORRECTION

PATENT NO.       : 6,958,325 B2  
APPLICATION NO.  : 10/044538  
DATED            : October 25, 2005  
INVENTOR(S)      : Abraham J. Domb Page 1 of 1

It is certified that error appears in the above-identified patent and that said Letters Patent is hereby corrected as shown below:

Claim 24, column 58, lines 8, replace "the" with --5--.

Signed and Sealed this

Seventh Day of August, 2007

JON W. DUDAS  
*Director of the United States Patent and Trademark Office*